(12) United States Patent
Romano et al.

(10) Patent No.: US 9,241,775 B2
(45) Date of Patent: Jan. 26, 2016

(54) ORTHODONTIC BRACKET AND METHOD

(75) Inventors: Rafi Romano, Herzlia (IL); Silvia Geron, Ramat-Efal (IL); Yuval Jacoby, Tel-Aviv (IL)

(73) Assignee: RGB Orthodontics Ltd., Tel-Aviv (IL)

( * ) Notice: Subject to any disclaimer, the term of this patent is extended or adjusted under 35 U.S.C. 154(b) by 279 days.

(21) Appl. No.: 12/921,159

(22) PCT Filed: May 21, 2009

(86) PCT No.: PCT/IL2009/000509
§ 371 (c)(1),
(2), (4) Date: Sep. 6, 2010

(87) PCT Pub. No.: WO2009/141825
PCT Pub. Date: Nov. 26, 2009

(65) Prior Publication Data
US 2011/0014583 A1    Jan. 20, 2011

Related U.S. Application Data

(60) Provisional application No. 61/071,887, filed on May 22, 2008.

(51) Int. Cl.
*A61C 3/00*     (2006.01)
*A61C 7/28*     (2006.01)
*A61C 7/14*     (2006.01)
*A61C 7/30*     (2006.01)

(52) U.S. Cl.
CPC . *A61C 7/28* (2013.01); *A61C 7/143* (2013.01); *A61C 7/303* (2013.01)

(58) Field of Classification Search
CPC ............ A61C 7/143; A61C 7/28; A61C 7/00; A61C 7/12; A61C 7/303
USPC ................. 433/8–11, 17, 12, 14, 16
See application file for complete search history.

(56) References Cited

U.S. PATENT DOCUMENTS

| | | | | |
|---|---|---|---|---|
| 3,193,930 A | * | 7/1965 | Bien | 433/15 |
| 3,421,221 A | * | 1/1969 | Silverman et al. | 433/8 |
| 4,322,206 A | * | 3/1982 | Reynolds | 433/9 |
| 4,531,911 A | * | 7/1985 | Creekmore | 433/8 |
| 4,669,980 A | * | 6/1987 | Degnan | 433/8 |
| 4,674,978 A | * | 6/1987 | Acevedo | 433/8 |
| 5,154,606 A | * | 10/1992 | Wildman | 433/8 |
| 5,374,187 A | * | 12/1994 | Vashi | 433/8 |
| 5,474,444 A | * | 12/1995 | Wildman | 433/8 |

(Continued)

FOREIGN PATENT DOCUMENTS

WO    WO 2009/141825    11/2009

OTHER PUBLICATIONS

International Search Report and the Written Opinion Dated Sep. 29, 2009 From the International Searching Authority Re.: Application No. PCT/IL09/00509.

(Continued)

*Primary Examiner* — Cris L Rodriguez
*Assistant Examiner* — Mirayda A Aponte

(57) ABSTRACT

Various designs of dental orthodontic brackets are described. Some brackets are self-ligating with no moving parts. Some brackets include multiple pathways for wires so an amount and type of force applied by the bracket can be varied without moving the bracket. Optionally, a same bracket is used for an entire orthodontic process.

42 Claims, 30 Drawing Sheets

(56) References Cited

U.S. PATENT DOCUMENTS

| | | | |
|---|---|---|---|
| 5,607,299 A * | 3/1997 | Nicholson | 433/3 |
| 5,711,666 A | 1/1998 | Hanson | |
| 6,071,119 A | 6/2000 | Christoff et al. | |
| 6,280,185 B1 * | 8/2001 | Palmer et al. | 433/8 |
| 6,302,688 B1 | 10/2001 | Jordan et al. | |
| 6,358,045 B1 | 3/2002 | Farzin-Nia et al. | |
| 6,682,345 B2 * | 1/2004 | Kesling et al. | 433/8 |
| 6,733,286 B2 | 5/2004 | Abels et al. | |
| 7,175,428 B2 * | 2/2007 | Nicholson | 433/11 |
| 7,306,457 B2 | 12/2007 | Vigolo | |
| 2001/0038991 A1 * | 11/2001 | Nicola et al. | 433/8 |
| 2002/0034715 A1 | 3/2002 | Hanson | |
| 2003/0064342 A1 * | 4/2003 | Fukutomi | 433/8 |
| 2003/0113682 A1 | 6/2003 | Pospisil et al. | |
| 2004/0072120 A1 | 4/2004 | Lauren | |
| 2005/0019719 A1 | 1/2005 | Hanson | |
| 2006/0204917 A1 * | 9/2006 | Clor | 433/10 |
| 2006/0228664 A1 * | 10/2006 | Castner et al. | 433/11 |
| 2006/0246392 A1 | 11/2006 | Vigolo | |
| 2006/0257810 A1 | 11/2006 | Maijer et al. | |
| 2007/0259300 A1 | 11/2007 | McLaughlin et al. | |
| 2008/0014544 A1 | 1/2008 | Nucera | |

OTHER PUBLICATIONS

Damon "The Damon Low-Friction Bracket: A Biologically Compatible Straight-Wire System", JCO-Online, 32(11): 670-680, 1998.

Eberting et al. "Treatment Time, Outcome, and Patient Satisfaction Comparisons of Damon and Conventional Brackets", Clinical Orthodontics and Research, 4: 228-234, 2001.

Harradine "Self-Ligating Brackets and Treatment Efficiency", Clinical Orthodontics and Research, 4: 220-227, 2001.

Harradine et al. "The Clinical Use of Activa Self-Ligating Brackets", American Journal of Orthodontics and Dentofacial Orthopedics, 109(3): 319-328, Mar. 1996.

Henao et al. "Evaluation of the Frictional Resistance of Conventional and Self-Ligating Bracket Designs Using Standardized Archwires and Dental Typodonts", Angle Orthodontist, 74(2): 202-211, 2004.

Kesling "Dynamics of the Tip-Edge Bracket", American Journal of Orthodontics and Dentofacial Orthopedics, 96: 16-25, 1989.

Kojima et al. "Numerical Simulation of Canine Retraction by Sliding Mechanics", American Journal of Orthodontics and Dentofacial Orthopedics, 127(5): 542-551, 2005.

Kojima et al. "The Effects of Friction and Flexural Rigidity of the Archwire on Canine Movement in Sliding Mechanics: A Numerical Simulation With a 3-Dimensional Finite Element Method", American Journal of Orthodontics and Dentofacial Orthopedics, 130: 275. el-275.e10, 2006.

Melsen "Biological Reaction of Alveolar Bone to Orthodontic Tooth Movement", The Angle Orthodontist, 69(2): 151-158, 1999.

Rinchuse et al. "Self-Ligating Brackets: Present and Future", American Journal of Orthodontics and Dentofacial Orthopedics, 132: 216-222, 2007.

Tanne et al. "Three-Dimensional Finite Element Analysis for Stress in the Periodontal Tissue by Orthodontic Forces", American Journal of Orthodontics and Dentofacail Orthopedics, 92: 499-505, 1987.

Von Böhl et al. "Changes in the Periodontal Ligament After Experimental Tooth Movement Using High and Low Continuous Forces in Beagle Dogs", Angle Orthodontist, 74(1): 16-25, 2004.

Von Böhl et al. "Focal Hyalinization During Experimental Tooth Movement in Beagle Dogs", American Journal of Orthodontics and Dentofacial Orthopedics, 125: 615-623, 2004.

Chen et al. "Systematic Review of Self-Ligating Brackets", American Journal of Orthodontics and Dentofacial Orthopedics, 137(6): 726e1-726e18, Jun. 2010.

International Preliminary Report on Patentability Dated Dec. 2, 2010 From the International Bureau of WIPO Re. Application No. PCT/IL2009/000509.

* cited by examiner

ORTHODONTIC BRACKET AND METHOD

RELATED APPLICATIONS

This Application is a National Phase of PCT Patent Application No. PCT/IL2009/00509 having International filing date of May 21, 2009, which claims the benefit of U.S. Provisional Patent Application No. 61/071,887 filed on May 22, 2008. The contents of the above Applications are all incorporated herein by reference.

FIELD AND BACKGROUND OF THE INVENTION

The present invention, in some embodiments thereof, relates to an orthodontic bracket and, more particularly, but not exclusively, to a bracket with no moving parts.

Orthodontic tooth movement is commonly generated by prolonged pressure applied to a tooth. It is generally believed that the tooth movement results from a cascade of events initiated by mechanical forces which alter the stress-strain distribution within the periodontal ligament (PDL) and results in remodeling of the surrounding alveolar bone, bone resorption occurs in areas of pressure and bone formation occurs in areas of tension.

An excessive orthodontic force produces hyalinization of the PDL and undermines bone resorption, impeding efficient bone remodeling. This phenomenon suggests that there is a maximum stress above which the bone remodeling rate decreases. The application of light and continuous forces results in reduced hyalinization, direct bone resorption, and relatively rapid tooth movement. It has been hypothesized that the key factor is not the absolute magnitude of the delivered force that is important, but rather, the distributed load or stress in the surrounding periodontal ligament and resultant strain.

In general, the following directions of force (as applied to teeth) are recognized:

Buccal—force applied away from the inside the mouth.
Palatal—force applied towards the inside of the mouth.
Mesial—force, in a direction along the dental arch, towards the front of the mouth.
Distal—force, in a direction along the dental arch, towards the back of the mouth.
Apical—force applied towards the apex of the roots of a tooth.
Incisor—force applied towards the edge of the crown of a tooth.
Tipping—force which moves the crown more than the root
Torque—force which moves the root more than the crown
Upright force which makes a tooth more perpendicular to gum
Translation—force which moves a tooth along the gum.
Rotation—tooth is rotated around an axis connecting its root and its crown.

In typical orthodontic situations, multiple teeth need to be moved and have their orientation changed. A standard way of achieving such multiple movements, is to attach a bracket to each of a plurality of teeth (at a buccal side or a palatal side) and interconnect the brackets using a wire. The wire and optional springs/elastic bands, apply the tooth correction forces. Additional plates, or other tools may be necessary to achieve the desired balance of forces on the teeth, a snot all forces can currently be applied using brackets.

In a typical methodology, the brackets are carefully attached so that they would be aligned if the teeth were aligned and a wire connected to the brackets in a manner where it can slide (no friction). This step of positioning the brackets is considered very important as it is generally undesirable to reconnect brackets due to misplacement and also undesirable to not align the teeth due to bracket misplacement. This wire applies forces as it tries to straighten, for example, due to its bending by relative positions of brackets on neighboring teeth. Translation forces may be applied using springs between teeth (brackets). After some time, the teeth move and the wire cannot apply significant force. At this time, the old wire is removed and a wire which is thicker is used, and which is better coupled to the bracket, for example, it may be rigidly held by friction in the bracket. This allows the wire to apply greater forces than the first wire and thus achieve the final small corrections to completely align the teeth. It is currently accepted that with friction based movement, lower rates of teeth alignment are achieved.

While the wire may be attached to the bracket using various tying mechanisms, it has become common to use self-ligating brackets. Active self ligating brackets are those with a spring clip that can press against the archwire. Passive self-ligating brackets are brackets in which the clip, ideally, does not press against the wire and is comparable to a buccal tube.

As a generalization, self-ligating brackets show excellent performance in vitro with smaller wires that are used early in treatment. However, when larger wires were used such as 0.016×0.022 in and 0.019×0.025 in nickel-titanium in the austenitic phase, no differences were found between self-ligating brackets and conventional brackets. Self-ligating brackets demonstrated low frictional resistance only up to certain size archwires in a 0.022-in slot.

Several investigators and many clinicians reported difficulties in finishing cases with self-ligating brackets. Particularly, torque, tip and rotation control can be compromised due to the greater play of the archwire in the slot of self-ligating brackets.

It should be noted that some visits during a treatment relate to failure of the moving parts of the self-ligating brackets, however, this is commonly considered a worthwhile tradeoff.

Many brackets have been developed with various design tradeoffs.

In the following US patents, self-ligating orthodontic brackets were described: U.S. Pat. No. 7,306,457 to Vigolo; U.S. Pat. No. 6,682,345 to Kesling et. al; U.S. Pat. No. 6,733,286 to Abels et. al; U.S. Pat. No. 6,358,045 to Farzin-Nia et. al; U.S. Pat. No. 6,302,688 to Jordan et. al; U.S. Pat. No. 6,071,119 June 2000 Christoff et. al and U.S. Pat. No. 5,711,666 to Hanson. US publication 20020197581 to Georgakis, Evangelos G.; et. al; also described a self-ligating bracket.

The following articles describe various properties of existing and hypothesized future brackets:
1. Von Bohl M M J, Von Den Hoff J W, A M. K-J. Focal hyalinization during experimental tooth movement in beagle dogs. Am J Orthod Dentofac Orthop 2004; 125:615-623.
2. Von Bohl M M J, Von Den Hoff J W, A M. K-J. Changes in the periodontal ligament after experimental tooth movement using high and low continuous forces in beagle dogs. Angle Orthod 2004; 74:16-25.
3. Melsen B. Biological reaction of alveolar bone to orthodontic tooth movement. Angle Orthod 1999; 69:151-158.
4. Reitan K. Biomechanical principles and reactions. In: Graber T M S B, editor. Orthodontics, Current Orthodontic Concepts and Techniques. St Louis: The C.V. Mosby Co.; 1985. p. 101-192.
5. Burstone C. The biphysics of bone remodeling during orthodontics-optimal force considerations. In: Norton L A, C J. B, editors. The Biology of Tooth Movement. Boca Raton: CRC Press; 1986. p. 321-333.
6. Tanne K, Sakuda M, Burstone C. Three dimensional finite element analysis for stress in the periodontal tissue by orthodontic forces. Am J Orthod Dentofac Orthop 1987; 92:499-505.
7. Kesling P C. Dynamics of the tip-edge bracket. Am J. Orthod. 1989; 96:16-28.
8. Damon D H. The Damon low-friction bracket: a biologically compatible straight-wire system. J Clin Orthod. 1998; 32:670-680.
9. Kojima Y, Fukui H., Miyajimac K., The effects of friction and flexural rigidity of the archwire on canine movement in sliding mechanics: A numerical simulation with a 3-dimensional finite element method. Am J Orthod Dentofac Orthop 2006:130, 3; 275.-275
10. Kojima Y, Fukui H. Numerical simulation of canine retraction by sliding mechanics. Am J Orthod Dentofacial Orthop. 2005; 127:542-551
11. Henao S P, Kusy R P. Evaluation of the frictional resistance of conventional and self-ligating bracket designs using standardized archwires and dental typodonts. Angle Orthod. 2004; 74:202-211
12. Rinchuse D. Ja, Miles B P G., Self-ligating brackets: Present and future Am J Orthod Dentofacial Orthop 2007; 132:216-22
13. Miles P G. SmartClip versus conventional twin brackets for initial alignment: Is there a difference?. Aust Orthod J. 2005; 21:123-127
14. Harradine N W T. Self-ligating brackets and treatment efficiency. Clin Orthod Res. 2001; 4:220-227.
15. Eberting J J, Straja S R, Tuncay O C. Treatment time, outcome, and patient satisfaction comparisons of Damon and conventional brackets. Clin Orthod Res. 2001; 4:228-234.
16. Harradine N W T, Birnie D J. The clinical use of Activa brackets. Am J Orthod Dentofacial Orthop. 1996; 109:319-328

The disclosures of all of the above articles, patents and publications are incorporated herein by reference.

SUMMARY OF THE INVENTION

The present invention, in some embodiments thereof, relates to a self-ligating bracket with no moving parts. In some embodiments, a plurality of wire holding and/or a plurality of force application areas are provided. This can provide flexibility in force application, as well as novel force application methods.

There is provided in accordance with an exemplary embodiment of the invention a self-ligating orthodontic bracket including a plurality of self-ligating wire guide channels with no moving parts, wherein said channels are arranged so that said bracket can selectively provide a tooth movement function selected from a group including at least two of tipping, rotation, angulation and torque to a tooth on which said bracket is mounted by varying a location of at least one wire between the guide channels and anchoring the at least one wire off of said tooth.

In an exemplary embodiment of the invention, said channels are arranged to provide at least two different values of at least one of said tooth movement functions, without moving the bracket and by moving the wire. Optionally, said bracket provides two different non-zero values for at least two of said tooth movement functions.

In an exemplary embodiment of the invention, said bracket provides at least three tooth movement functions using self-ligating channel guides.

In an exemplary embodiment of the invention, at least two of said channels are formed from a split self ligating wire guide, wherein each portion of said guide is self-ligating. Optionally, said two portions do not share a common axis. Optionally or alternatively, said two portions are separated by a slot and wherein said slot is wide enough for a stainless steel wire that self ligates in the a guide channel portion to bend and exit through. Optionally, a guide wire portion has a wing forming at least one boundary thereof and wherein said wing defines at least one depression formed in said wing outside of said channel.

In an exemplary embodiment of the invention, at least one of said wire guide channels has a wire insertion direction substantially parallel to said tooth surface. Optionally, said wire guide includes an interference element which extends substantially perpendicular to said tooth surface.

In an exemplary embodiment of the invention, at least one of said wire guide channels has a wire insertion direction substantially away from said surface.

In an exemplary embodiment of the invention, for at least one of said wire guide channels a wire remains substantially parallel to a gum line during insertion.

In an exemplary embodiment of the invention, said plurality of channels are positioned to function as an incisial channel and as a buccal channel.

In an exemplary embodiment of the invention, said at least one of said wire guide channels has a wire insertion direction and an interference element which forms a boundary of a side of said channel in said direction. Optionally, said interference element blocks less than 80% of a width of said side. Optionally, said blocking is less than 50%. Optionally said blocking is less than 30%. Optionally, said blocking is less than 20%. Optionally, said blocking is less than 10%.

In an exemplary embodiment of the invention, a length of said interference element where it blocks said wire insertion direction is less than 80% of a functional length of said channel, within which said wire lies. Optionally, said length is less than 50% of said functional length. Optionally, said length is less than 30% of said functional length.

In an exemplary embodiment of the invention, said channel has a first axial portion bounded on three sides and a second axial portion not substantially overlapping with said first axial portion wherein sad interference element lies.

In an exemplary embodiment of the invention, the bracket comprises an inclined segment positioned for guiding said wire up and past said interference element into said channel.

In an exemplary embodiment of the invention, said bracket defines at least one recess for positioning a tool between said wire and said bracket while said wire is self-ligated.

In an exemplary embodiment of the invention, said first axial portion is less than 80% of a length of said channel. Optionally, said first axial portion is less than 50% of a length of said channel.

In an exemplary embodiment of the invention, a single self-ligating mechanism is shared by at least two wire guide channels sections. Optionally, said self-ligating mechanism is an interference element.

There is provided in accordance with an exemplary embodiment of the invention a self-ligating orthodontic bracket including a plurality of self-ligating wire guide channels with no moving parts, wherein said channels are arranged to include a first self-ligating channel on a left side of said bracket and a second self-ligating channel on a right side of said bracket. Optionally, said channels are not on a centerline of said bracket. Optionally or alternatively, said channels are angulated.

There is provided in accordance with an exemplary embodiment of the invention a self-ligating orthodontic bracket including a plurality of self-ligating wire guide channels with no moving parts, wherein each said channel has a first axial portion bounded on three sides and a second axial portion not substantially overlapping with said first axial portion wherein an interference element that blocks a fourth cardinal direction of said channel, lies.

There is provided in accordance with an exemplary embodiment of the invention an orthodontic bracket for a tooth, comprising at least one self-ligating channel with no moving parts and which allows movement of a wire retained by said channel, wherein said channel has a substantially uniform width in a direction parallel to the tooth along at least 40%, 60%, 80% or intermediate or greater parts of said channel.

There is provided in accordance with an exemplary embodiment of the invention an orthodontic bracket for a tooth, comprising at least one self-ligating channel for retaining a wire, which channel includes a wire retainer with no moving parts which resists exit of wire from said channel during regular orthodontic use, said retainer requiring a distortion of said wire by less than 30% off axis for entry or exit into said channel. Optionally, said channel includes a guide shape which guides a wire into said channel. Optionally or alternatively, said wire retainer comprises at least one projection which requires a distortion of said wire to pass said projection into or out of said channel. Optionally, said distortion comprises a distortion within a length of said channel.

In an exemplary embodiment of the invention, said wire retainer comprises at least labyrinth-like passageway out of said channel.

In an exemplary embodiment of the invention, said channel is designed for a rigid wire.

In an exemplary embodiment of the invention, said channel includes an interference element which prevents wire escape from the channel, which interference element does not lie over the entire axial extent of the channel.

There is provided in accordance with an exemplary embodiment of the invention an orthodontic bracket for a tooth, comprising at least one self-ligating channel with no moving parts and comprising at least one friction-type channel.

There is provided in accordance with an exemplary embodiment of the invention an orthodontic bracket for a tooth, comprising at least one channel defined by at least one side-wall, said channel being split into at least two portions and said sidewall including at least one recess formed as a wire guide, such that a wire can lie inside a channel portion and held against said wire guide.

There is provided in accordance with an exemplary embodiment of the invention an orthodontic bracket for a tooth, comprising at least one channel defined by at least one side-wall, said sidewall including at least one recess formed as a wire guide, said wire guide being generally open in a direction generally buccally.

There is provided in accordance with an exemplary embodiment of the invention an orthodontic bracket for a tooth, comprising at least one channel having a side open over at least 30% of its length to a buccal or incisorial side.

There is provided in accordance with an exemplary embodiment of the invention an orthodontic bracket for a tooth, comprising at least three channels each suitable for simultaneously retaining wire therein without moving parts. Optionally, a same wire can lie in two of said channels simultaneously. Optionally or alternatively, at least two of said channels are self-ligating.

There is provided in accordance with an exemplary embodiment of the invention an orthodontic bracket for a tooth, comprising at least two self-ligating channels which can be occupied simultaneously with separate wires.

There is provided in accordance with an exemplary embodiment of the invention a method of manipulating a tooth during orthodonty, comprising:
  (a) attaching a bracket to the tooth;
  (b) running at least two wires through said bracket; and
  (c) positioning said wires so that they together apply movement forces to said tooth. Optionally, at least one of said wires is attached to said bracket using a self-ligating channel.

There is provided in accordance with an exemplary embodiment of the invention an orthodontic bracket for a tooth, having at least two self-ligating wire channels or portions, each suitable for retaining a wire, defined therein and wherein said channels are not parallel to each other. Optionally, said channels comprise a split channel, each part of which can act as a channel. Optionally or alternatively, one of said channels is a straight channel and another of said channels is a split channel with two different angulations for each wire retaining channel portion thereof.

There is provided in accordance with an exemplary embodiment of the invention a method of manipulating a tooth during orthodonty, comprising:
  (a) attaching a bracket to the tooth;
  (b) running at least two wires through said bracket; and
  (c) positioning said wires so that one wire activates a root of said tooth and one wire maintains an alignment of said tooth with other teeth.

There is provided in accordance with an exemplary embodiment of the invention an orthodontic bracket, comprising a plurality of at least three self-ligating individually usable wire retainers. Optionally, said bracket comprises at least four such wire retainers.

There is provided in accordance with an exemplary embodiment of the invention an orthodontic self-ligating bracket, having a plurality of wire passageways defined therein, which passageways define at least 4 different wire configurations. Optionally, said passageways define at least 8 different wire configurations.

There is provided in accordance with an exemplary embodiment of the invention an orthodontic self-ligating bracket, having at least one self-ligating wire channel on a left side and at least a second self-ligating channel on aright side thereof. Optionally, the bracket comprises at least two self-ligating channels on each of said right and left sides.

There is provided in accordance with an exemplary embodiment of the invention an orthodontic self-ligating bracket, having at least one self-ligating wire channel configured to hold a wire in a manner not parallel to a surface of a tooth.

There is provided in accordance with an exemplary embodiment of the invention a method of rotating a tooth during orthodonty, comprising:
  (a) attaching a bracket to the tooth; and
  (b) running a wires through said bracket along a path that is either or both not parallel to a surface of the tooth and includes sections at different distances from said tooth.

There is provided in accordance with an exemplary embodiment of the invention an orthodontic bracket, comprising a plurality of tie wings adapted for mounting an elastic module thereon, at least two of said plurality of tiewings including an angulated portion, that is at an angle to vertical and horizontal axes of said bracket.

Optionally, said angulated portion is provided as a broadening of said tiewing.

There is provided in accordance with an exemplary embodiment of the invention a method of orthodonty, comprising:

(a) providing a case where a friction wire is needed for standard brackets;

(b) treating said case to provide tooth alignment using only self-ligated bracket channels of a plurality of brackets or to a point where a rectangular friction wire can be mounted on said brackets by fitting into a suitable slot therein.

There is provided in accordance with an exemplary embodiment of the invention a method of orthodonty, comprising:

(a) providing a case where a standard bracket needs to be relocated after a time;

(b) treating said case to provide tooth alignment without relocating any bracket.

There is provided in accordance with an exemplary embodiment of the invention a bracket set comprising a plurality of brackets with mounting material on a base thereof and each including at least one self-ligating channel with no moving parts and at least one wire threaded through the brackets, such that said channels through which the wire is threaded do not all lie on a same plane.

There is provided in accordance with an exemplary embodiment of the invention a method of orthodonty, comprising:

(a) aligning a plurality of teeth;

(b) providing active retention to said teeth using a plurality of brackets mounted on a lingual side of said teeth with a wire mounted on said brackets.

There is provided in accordance with an exemplary embodiment of the invention a self-ligating orthodontic bracket including a plurality of wire guide channels, wherein said channels are arranged so that said bracket can selectively provide a tooth movement function selected from a group including at least two of tipping, rotation, angulation and torque to a tooth on which said bracket is mounted by varying a location of at least one wire between the guide channels and anchoring the at least one wire off of said tooth, said channels are arranged to provide at least two different values of at least one of said tooth movement functions, without moving the bracket and by moving the wire.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Overview

Figure 1A:
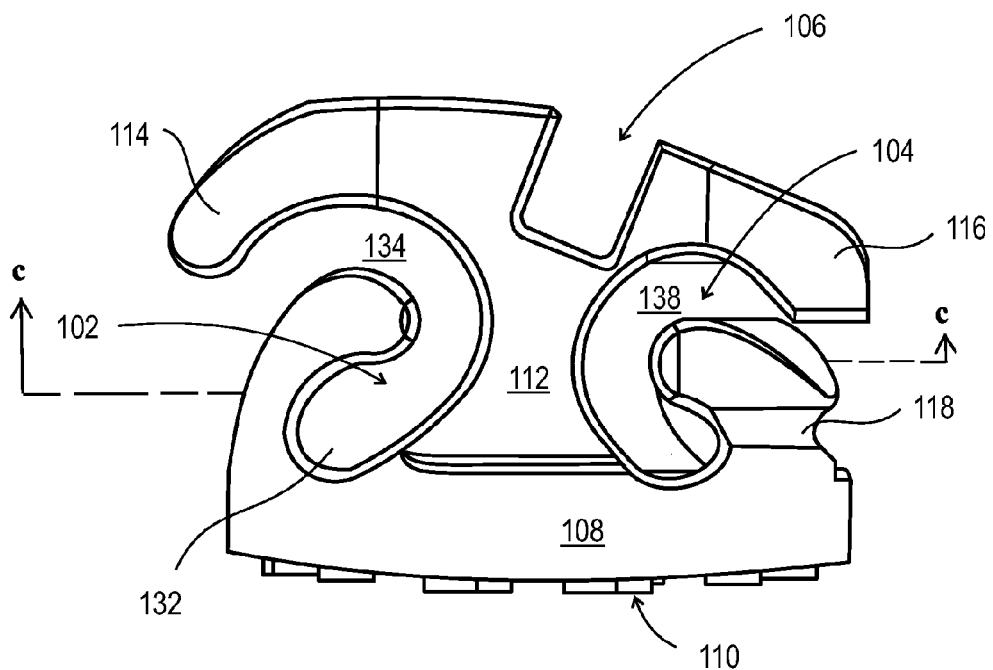
FIG. 1A is a side view of a bracket in accordance with an exemplary embodiment of the invention.

The present invention, in some embodiments thereof, relates to orthodontic bracket and, more particularly, but not exclusively, to self-ligating brackets with no moving parts.

As will be described in more detail below, what is presented, includes novel methods of holding a wire in a bracket with reduced friction, novel bracket designs and novel methods of orthodontic force applications. Not all of these need be provided in any particular embodiment of the invention. In addition, as will also be exemplified below, various of these features may be combined with brackets of the art, to potentially provide useful functionality.

In general, a bracket according to some embodiments of the invention, includes one or more self-ligating wire holding channels with no moving parts, optionally split and one or more wire guides, which guide wires to apply desired forces to a tooth via the bracket. In some embodiments, one or more elastic tiewings are provided. In an exemplary embodiment of the invention, the forces include two or more of angulation, rotation, torque and tipping.

In an exemplary embodiment of the invention, when a tooth movement function, such as a change in angle or change in position is provided by the bracket, the bracket allows at least two non-zero levels of change to be applied by a same bracket without moving the bracket, but rather moving the wire. This can allow, for example, applying a force that tends to overcorrection and then repositioning the wire so as to stop the force.

In a particular, non-limiting embodiment of the invention, described in greater detail below, the bracket includes 3 different channels with versatile ligation, regular and self-ligating type, optionally with selective enhanced tipping control, as follows:

a) An incisal channel, optionally used for initial alignment for resilient small dimension archwires with a labyrinth-like type entry to enable non-friction movements.

b) A standard edgewire straight wire channel for larger dimension wires for advanced tip and torque control.

c) A gingival channel with snail-shape type entry, optionally bi-angulated for angulation control.

Optionally, bracket tiewings are rounded, have widened ends and/or angulated outwards to ease ligation and/or reduce inadvertent release of elastics.

In an exemplary embodiment of the invention, the bracket does not have any sliding or moving elements that can break or become damaged. The orthodontic brackets may comprise various materials such as plastic, metal or ceramic and may be manufactured in various bracket sizes, optionally with tooth adapted bracket pads for the labial and/or lingual surfaces and different channel dimensions. In an exemplary embodiment of the invention, the bracket can be adjusted by a dentist, for example, using a burr, for example, before or after attachment to a tooth.

A particular feature of some embodiments of the invention is that at least one of the wire holding channels includes at least one wire retaining mechanism. In an exemplary embodiment of the invention, the wire retaining mechanism comprises an asymmetric mechanism which supports relatively easier entry of wire into the retaining mechanism and more difficult removal of the wire. In an exemplary embodiment of the invention, the difficulty lies not with degree of forces, but rather with probability of suitable manipulation of wire occur while the wire is in orthodontic use. In an exemplary embodiment of the invention, the wire retaining comprises a labyrinth like structure including a work volume and a passage to the volume, for example, in the form of a spiral with the working area (activation zone) substantially at the inside end/center of the spiral. Optionally, the passage is defined so that there is no straight line vector for a wire within the working area to outside of the labyrinth-like retainer. Optionally, this reduces the probability that random forces during use will cause a wire to ext the retainer.

In an exemplary embodiment of the invention, the labyrinth is divided into parts that are spread out along the channel. Optionally, the channel is transversely slotted and a wire retaining element is provided in the slot.

In an exemplary embodiment of the invention, a ramp or inclined section is provided to assist in guiding a wire into a channel. Optionally or alternatively, the incline is matched by one or more elements that deform the wire as the wire is pulled up the ramp.

In an exemplary embodiment of the invention, the channel defined by the working area has a substantially uniform diameter and/or cross-section along its length. Optionally or alternatively, the channel has a diameter of about 101%-180%, for example, 105%, 110%, 125%, 155% or intermediate percentages of the intended wire size(s). Optionally, the channel is split into two or three sections (e.g., by perpendicular slots which define wire guides) and each section is substantially uniform, as discussed.

In an exemplary embodiment of the invention, the passage is made shorter to require less wire manipulation. Optionally or alternatively, the activation zone is made small with respect to the direction of force application, so as to reduce wire movement inside the activation zone. Optionally or alternatively, the passage is oriented in a direction convenient for wire insertion and/or requiring a lesser amount of movement of a wire away from the teeth. Optionally or alternatively, the passage (e.g., near the work area and/or near its exit) is oriented in a manner that rejections wire exit in common wire motions. Optionally, the passage way opens buccally, rather than as shown. Optionally, a labyrinth of opposite spiraling direction is used, rather than as shown.

In an exemplary embodiment of the invention, a wire retainer is a distortion based retainer in which a wire is distorted (e.g., bent or twisted) when inserted into the retainer. Optionally, the distortions required are selected so that the probability of such distortion spontaneously occurring during regular orthodontic use is low. Optionally, this selection comprises a plurality of distortions required to happen at a same time to cause release of a wire. Optionally or alternatively, the retainer is designed to include one or more wire distortion guiding elements that cause distortion, when it occurs spontaneously, to be incompatible with release. Optionally or alternatively, the retainer includes one or more protrusions or recesses which guide distortion of the wire when entering, but which optionally act as a step which resists correct distortion when a wire is moved in a direction out of the retainer. Optionally or alternatively, the distortions are distortions in two directions, for example, both bending and twisting of the wire.

In an exemplary embodiment of the invention, the distortions move the wire during manipulation/distortion less than 2 mm. Optionally or alternatively, the movement of the wire is mainly inside the bracket and not outside the bracket. Optionally or alternatively, the wire is distorted less than 30%, 20%, 10%, 5%, 2% or intermediate amounts, where distortion percentage is defined as a change in wire shape, which when corrected for translation of the wire by the distortion, provides an overlap of 100% less the distortion percentage with the undistorted wire. Thus, for example, a wire that is rotated 90 degrees is distorted to a high percentage, while a wire that is translated at a point, is distorted only to the extent that the wire bends. In an exemplary embodiment of the invention, the distortion type is selected so as not to plastically deform the wire to a significant degree. Optionally or alternatively, the distortion is selected to require an elongation of any part of the wire of less than 30%, 20%, 12%, 10%, 5% 3% or intermediate amounts.

In an exemplary embodiment of the invention, a wire retainer includes at least one portion that when a wire is pressed against, prevent movement of the wire towards an exit of the retainer, absent an additional motion. Optionally, the additional motion is in a direction at having an angle of at least 50°, 80°, 90°, 120°, 180° or intermediate angles away form the exit of the wire retainer.

It is a particular feature of some embodiments of the invention that a bracket includes a plurality of different wire-bracket interactions, including, for example, multiple wires, angulation control, rotation, tipping and torque. In an exemplary embodiment of the invention, a plurality of pathways, for example, at least 4, at least 6, at least 8 or more different paths for a same wire on a bracket is provided.

In an exemplary embodiment of the invention, the multiple interactions are provided by using small wire retainers, as compared to clips or ligations of the art. In an exemplary embodiment of the invention, a single channel includes two wire retainers, each of which is sufficient to hold a wire on its own, allowing the wire to continue outside of the channel. Optionally, a plurality of such multi-retainer channels are provided. Optionally or alternatively, at least three or at least four, or more individually usable wire retainers for thin wires are provided. In an exemplary embodiment of the invention, at least one wire retainer is provided for each quadrant of the bracket.

In an exemplary embodiment of the invention, the provision of multiple wire-bracket interactions allows greater flexibility in bracket placement and/or allows a greater and/or more exact force to be achieved. In one example, it is often the case that a standard bracket cannot provide effective force which mounted in its final position and therefore the bracket must be remounted during an orthodontic process. In an exemplary embodiment of the invention, a bracket in accordance with an exemplary embodiment of the invention can be used over a greater part or all of the process, as a wire is moved form one wire-bracket interaction state to another, as the orthodontic process progresses. Optionally or alternatively, a misaligned bracket may still be used to provide alignment of teeth, by choosing suitable wire-bracket interactions.

In an exemplary embodiment of the invention, the bracket can be used to apply low forces and large deflections and/or large forces using thin wires, even if the brackets are nearly aligned, for example, by choosing non-aligned bracket channels in adjacent teeth.

In an exemplary embodiment of the invention, at least one of the channels of a bracket is an angled channel. Optionally, a dual-angled channel is provided, I which each of at least two parts of a channel has a different angle. Optionally, by selecting only apart of the channel, different wire-bracket angles are achieved. Optionally or alternatively, different channels have different angulations or multiple angulations to the plane of occlusion and/or relative to other channels (e.g., straight channels that go the width of the bracket).

It is a particular feature of some embodiments of the invention that a bracket includes no moving parts and does not require any external parts for usage of any of its self ligating channels or wire retainers. In some embodiments, a frictionless retainer with no moving parts may be provided in a bracket that also includes a moving part for wire retention. In some embodiments, no moving parts are provided at all.

In an exemplary embodiment of the invention, the bracket as a whole is made of a single material, or a body thereof is made is made of a single material and a base of different composition. Optionally, one or more coatings are provided.

In an exemplary embodiment of the invention, the bracket is made in an atheistic manner.

In an exemplary embodiment of the invention, the bracket is formed of plastic, composite materials, dental structural materials or ceramic or metal. In an exemplary embodiment of the invention, the bracket is non-elastic. In an exemplary embodiment of the invention, the bracket is formed with or stained to have a color matching an underlying tooth.

In an exemplary embodiment of the invention, the openings to one or more of the wire holding channels face away form the opening of the mouth, thereby hiding wires when in use.

In an exemplary embodiment of the invention, the bracket is made thinner, in a buccal dimension, for example, by not needing to include room for an active or passive retaining element. In an exemplary embodiment of the invention, the bracket is thinner than self-ligating brackets, for example, on the order of 3 wire thicknesses, two wire thicknesses, 1.5 wire thicknesses and/or intermediate sizes.

In an exemplary embodiment of the invention, the bracket is used in a lingual side of the teeth. Optionally, the small size of the bracket supports its use for active retention.

It is a particular feature of some embodiments of the invention that a plurality of substantially parallel wire retaining channels are provided in a bracket. Optionally, at least one channel is not in use in some teeth and is in use in others.

It is a particular feature of some embodiments of the invention, that a single bracket includes both friction and non-friction wire retaining channels.

In an exemplary embodiment of the invention, the provision of multiple channels and/or multiple channel types and/or multiple wire retention points and/or multiple wire-bracket interaction types may allow for a reduced and/or more effective use of separate springs or elastic bands. In an exemplary embodiment of the invention, however, the bracket supports multiple methods of attaching an elastic band to a bracket, for example, one or more of orthogonally across a bracket and in a diagonal across the bracket.

In an exemplary embodiment of the invention, the edges of the labyrinth-like wire retainers serve as wings for holding elastic elements. In an exemplary embodiment of the invention, the wings are oblique, have a thickened end and/or curve down towards the tooth (e.g., serving as part of a labyrinth), which may assist in holding teeth.

It is a particular feature of some embodiments of the invention that novel force application methods are provided. In an exemplary embodiment of the invention, the use of one channel as a rail for tooth guiding motion supports more precise movement of teeth during alignment. For example, the use of two substantially parallel channels allows a translation of a tooth to be guided with less or no unintentional torque. Optionally or alternatively, bodily movement is thus supported without binding, as thin wires are less likely to bind and the provision of multiple channels supports movement with less tipping and thereby less binding. Optionally or alternatively, using two or three channels simultaneously supports applying torque to a tooth using the distance between two cannels for enhancing a moment of the force. This may allow the use of a thick wire to be avoided.

In an exemplary embodiment of the invention, channeling a wire along a path that change sin its buccal dimension, for example, from a first path portion at one buccal position to a second path at a second buccal position, supports tooth rotation, in place, for example around an axis substantially collinear with a tooth axis.

In an exemplary embodiment of the invention, channeling a wire along a path including two different incisal heights relative to a gum, supports torquing of the tooth.

It is a particular feature of some embodiments of the invention that a greater part of the teeth alignment is achieved using non-friction effects. In an exemplary embodiment of the invention, a sufficient portion of alignment is performed that insertion of a straightedge wire in a standard slot can be achieved without using an elastic band to urge the wire towards the slot. In an exemplary embodiment of the invention, at least 80%, at least 90%, at least 95% of alignment (e.g., as measured with respect to duration) with respect to angle correction and translation correction of the teeth is completed using thin wires. In some embodiments of the invention, all the alignment is achieved using thin wires.

In an exemplary embodiment of the invention, better force application is achieved, for example, because where there is less friction, the amount of force applied can be better calculated. Optionally, this allows a force closer to the maximum to be applied.

In an exemplary embodiment of the invention, the tooth alignment procedure is made faster, for example, by 20%, 30%, 40%, 60% or intermediate or greater percentages, for example, due to more correct application of force, as compared to an expected duration using a frictionless self-ligating slot or a friction slot.

Optionally or alternatively, the number of visits during an orthodontic procedure, is reduced, for example, by 20%, 30%, 50%, 60% or more.

Optionally or alternatively, additional visits are provided for adjustment of the wires, to make use of the faster alignment and/or more sophisticated force application enabled by some embodiments of the invention, for example, 30%, 40, 50% visits or more. Optionally, the number of visits remains substantially unchanged, with visits due to damaged brackets being replaced with visits for adjustment of a procedure in accordance with an exemplary embodiment of the invention.

Also provided in accordance with some embodiments of the invention are instruction sets showing how to apply various forces and/or software for planning orthodontic procedures taking into account the magnitudes and/or direction of forces achievable using brackets in accordance with exemplary embodiments of the invention.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIGS. 1A-1H illustrate a bracket 100 including labyrinth-like wire retainers, in accordance with an exemplary embodiment of the invention.

Figure 1B:
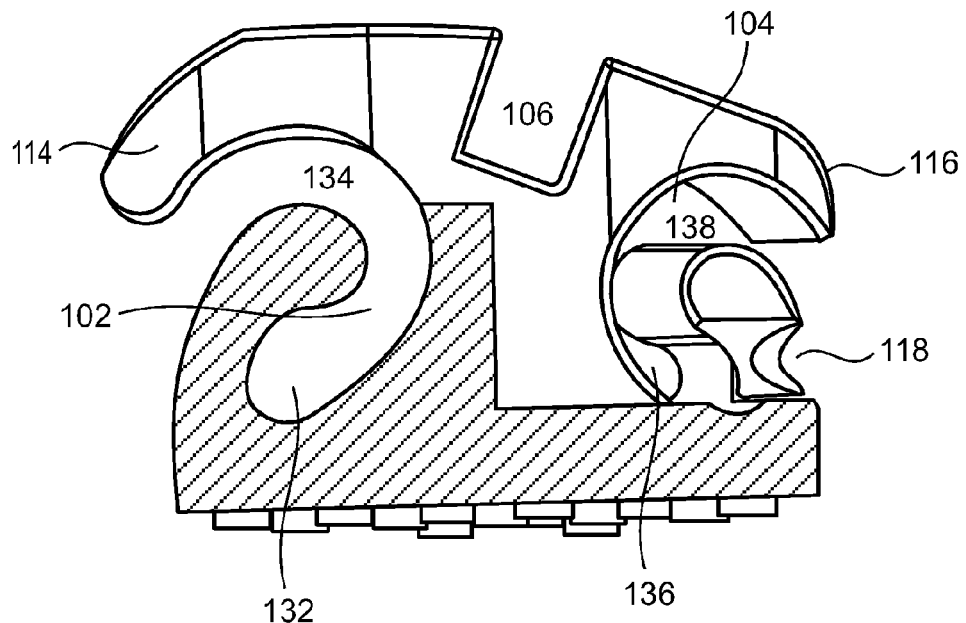
FIG. 1B is a cross-sectional view of the bracket of FIG. 1E, taken in the directions of line B-B therein, according to some embodiments of the invention.
Figure 1C:
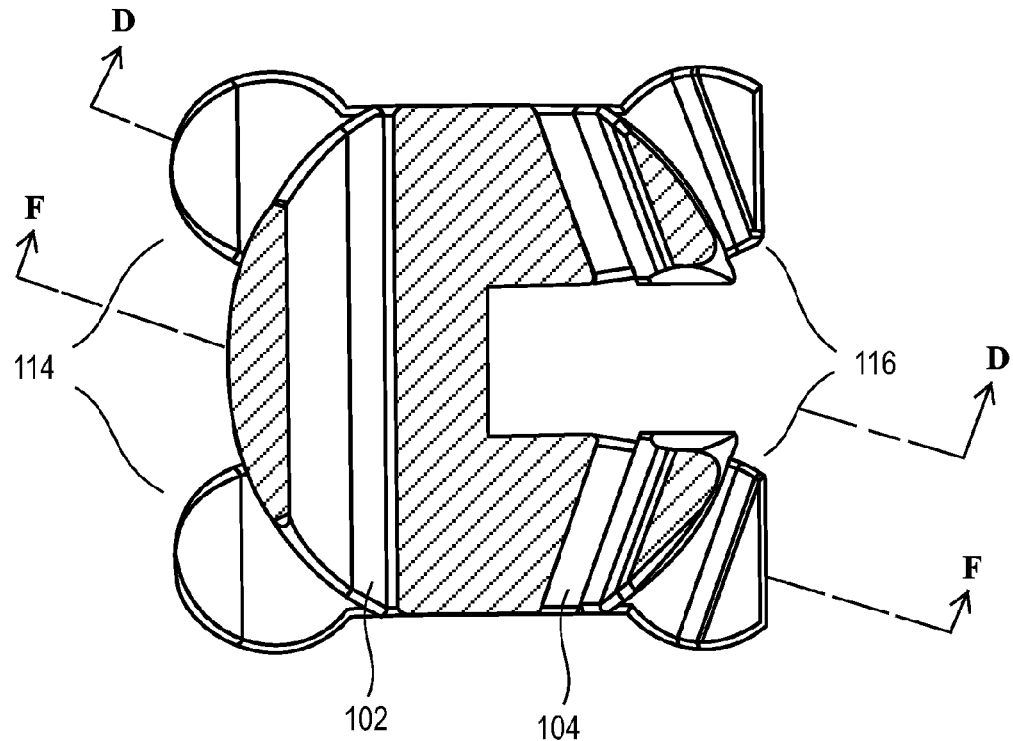
FIG. 1C is a cross-sectional view of the bracket of FIG. 1A, taken in the direction of line C-C therein, according to some embodiments of the invention.
Figure 1D:
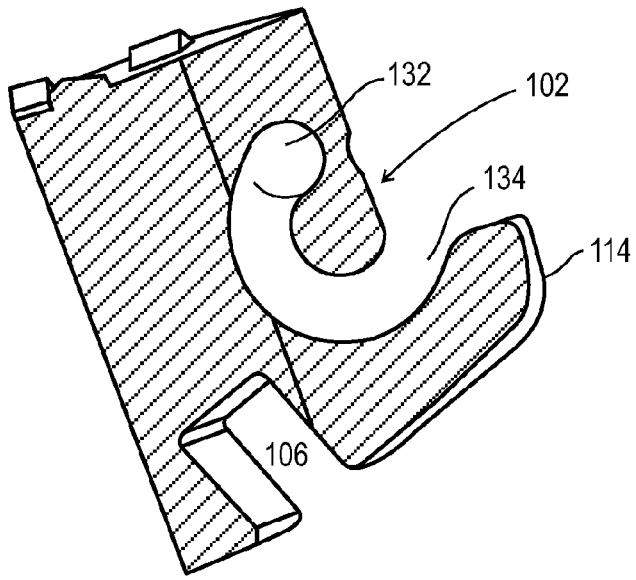
FIG. 1D is a cross-sectional view of the bracket of FIG. 1C, taken in the direction of line D-D therein, according to some embodiments of the invention.
Figure 1E:
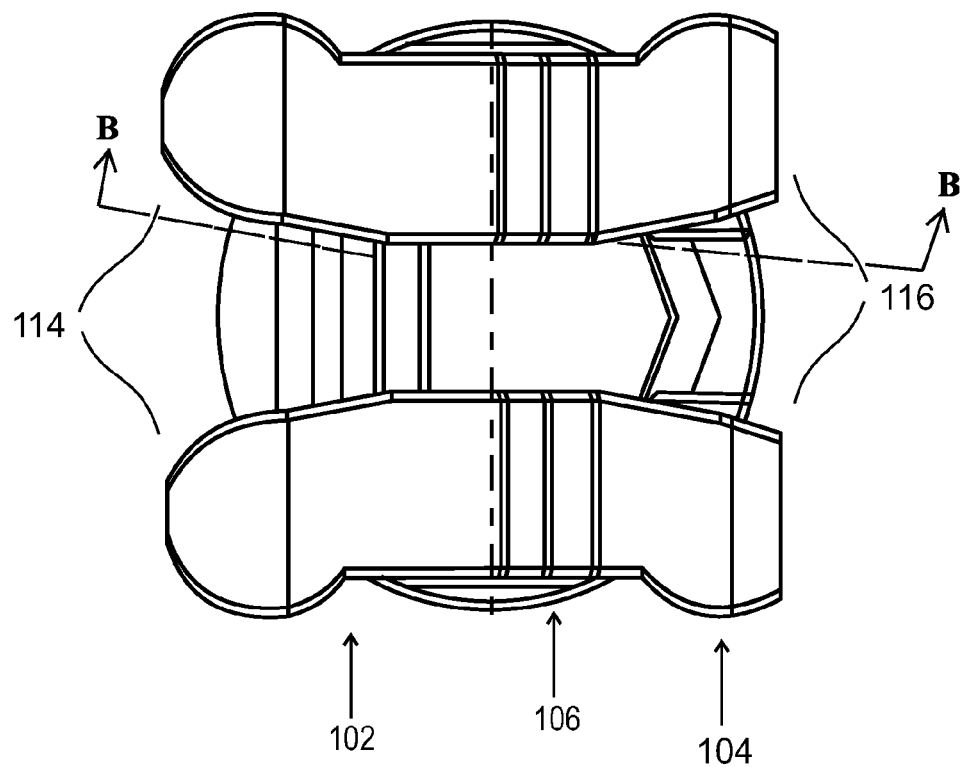
FIG. 1E is a top view of the bracket of FIG. 1A, according to some embodiments of the invention.
Figure 1F:
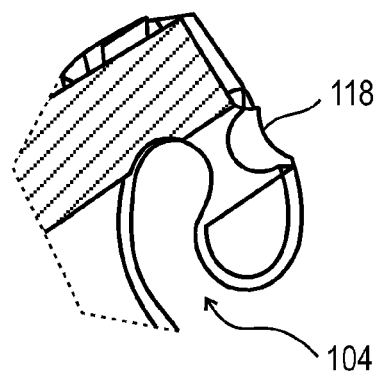
FIG. 1F is a cross-sectional view of a portion of the bracket of FIG. 1C, taken in the direction of line F-F therein, showing a detail of one of the labyrinth-like wire restrainers of the bracket, according to some embodiments of the invention.
Figure 1G:
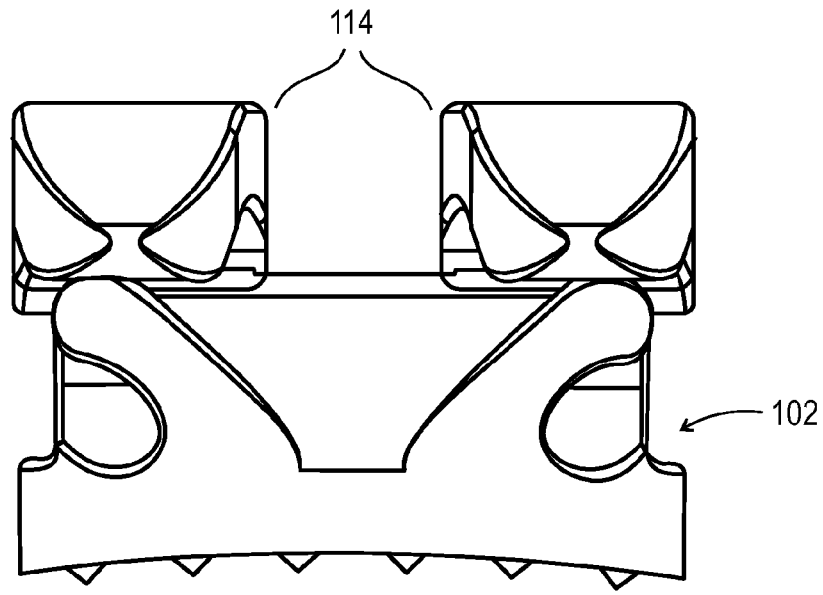
FIG. 1G is a front view of the bracket of FIG. 1A, according to some embodiments of the invention.
Figure 1H:
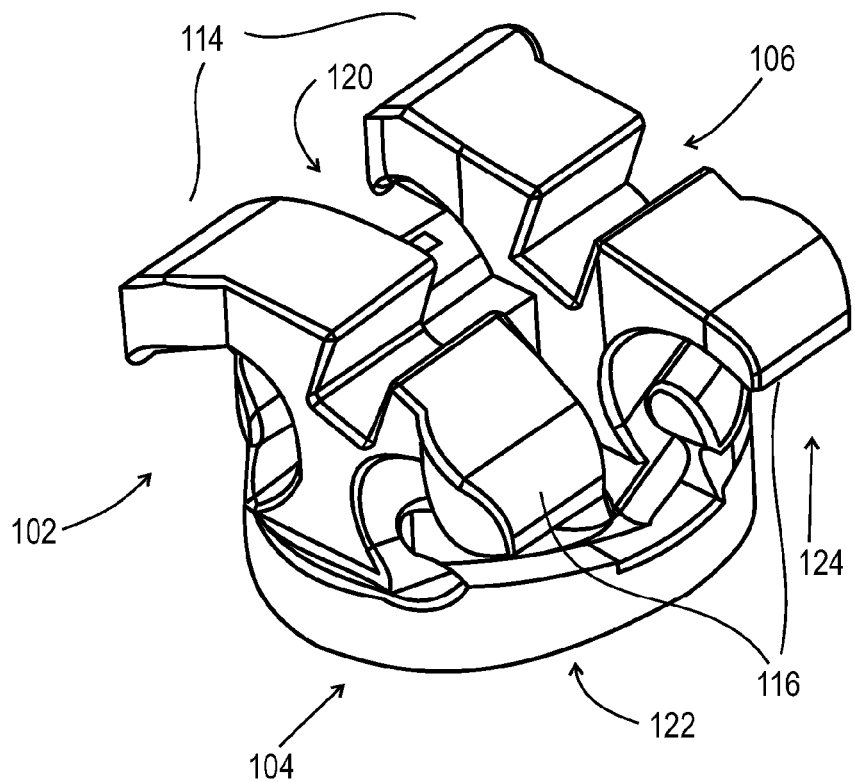
FIG. 1H is an isometric view of the bracket of FIG. 1A, according to some embodiments of the invention.

FIG. 1A is a side view of bracket 100. FIG. 1E is a top view of bracket 100. FIG. 1B is a view along line B-B in FIG. 1E. FIG. 1C is a view along line C-C in FIG. 1A. FIG. 1D is a view along line D-D in FIG. 1C. FIG. 1F is a view along line F-F of FIG. 1C, showing a detail of one of the labyrinth-like wire restrainers. FIG. 1G is a front view of bracket 100. FIG. 1H is an isometric view of bracket 100.

Referring back to FIG. 1A, a first self-ligating wire channel 102 is formed in a body 112 of bracket 100. Body 112 is mounted (optionally formed integrally with) a base 108, which may include a mounting design 110, for example, a plurality of protrusions. Optionally, base 108 has a concave surface, to match expected tooth shapes. Channel 102 includes a working area 132, where a flexible wire will rest and a passageway 134 leading to area 132. Optionally, passageway 134 is as wide or slightly wider than a diameter of any wire which is planned to be used. Optionally, the passageway width is 0.0142 inch and the working area diameter is 0.016 inch, optionally for a 0.014 inch diameter wire. An optional wing 114 optionally serves both as part of passageway 134 and as a holder for an elastic band. Optionally, as can be seen in the top view of FIG. 1E, the wings are rounded and/or angulated out and/or widen at their ends. Optionally or alternatively, as can be seen in front view of FIG. 1G the edges of the tiewings may curve downwards to assist in holding such elastic elements and/or to guide wires into the channels.

In the design shown, channel 102 is an incisal channel. In an exemplary embodiment of the invention, a gingival channel 104 is provided as well or instead, and includes a work area 136 and a passageway 138. Optionally, as shown in FIG. 1H, for example, channel 104 is split by a slot 120 (perpendicular or angulated) into a left channel section 122 and a right channel section 124. In an exemplary embodiment of the invention, each part of channel 104 has a different angle relative to the axis of channel 102. Optionally, the channels are generally parallel to the surface of the tooth but this may not be in some embodiments, for example, a channel may be split with each part angled towards the tooth and towards each other.

In an exemplary embodiment of the invention, channel 102 allows some slack of wire movement in the channel. Optionally, channel 104, by being angulated, better defines the position of some wire sizes and reduces such slack and/or reduces chance of wire release. Optionally or alternatively, such angulation provides additional activation (e.g., friction) on the wire, optionally to a known amount which is optionally selected by choosing a suitable wire diameter and/or one of the angulated channels.

In an exemplary embodiment of the invention, bracket 100 includes one or more wire guides 118, for example, formed on an outside surface of bracket 100, optionally positioned (as will be shown below) for guiding a wire to apply angulation forces. In an exemplary embodiment of the invention, such guides hold a wire but do not restrain it as do labyrinth-like channels 102 and 104. Optionally or alternatively, channel 106 (described below) and/or slot 120 are used as such a guide for thin wires.

In an exemplary embodiment of the invention, a standard straight edge channel 106 is provided for use with thick, rectangular wires. Optionally or alternatively, a different type of channel can be provided, for example, for a different shape wire (e.g., triangular cross-section) or as described below. Optionally, channel 106 is used with ligation elements for other shaped wires.

Following are exemplary features and/or properties of bracket 100, according to the above design. As noted and as will be exemplified below, not all brackets in accordance with an exemplary embodiment of the invention include all of the features/properties.

(a) Bracket 100 includes three channels and multiple wire pathways. Optionally, all three channels are occupied simultaneously. The multiple channels provide for various movements and/or for better tip and rotation control during different stages of treatment. In an exemplary embodiment of the invention, the incisal and gingival channels are designed for passive ligation for initial stages of treatment (up-to 0.016" size of wire). Optionally or alternatively, the incisal channel can be used for partial ligation to upright and over correct a specific tooth position. For example, using one of the angulated channels—partial ligation—provides wide range of movement in a certain required direction. In an exemplary embodiment of the invention, the middle channel is designed to fit the straight wire concept, optionally with conventional elastomeric or metal ties for improved torque control and better finishing.

In an exemplary embodiment of the invention, different channels are used for different purposes, for example, moving a tooth only in a direction that is needed. For example, a self ligating incisal channel is used for fast alignment, an angulated channel (gingival portion) is used for angulation control, and the edgewise channel is used for torque control, space closure and/or finishing.

In an exemplary embodiment of the invention, not matching channels in brackets of neighboring teeth are used with a shared wire, to apply greater (e.g., forces, moment) even when the teeth are close to being aligned. Optionally, the wire is moved out of the mismatching channels, before an over correction is achieved.

In an exemplary embodiment of the invention, the splitting of one, two or more channels by a slot allows a wire to lie only in part of a channel and/or travel in a direction generally perpendicular to the channel, along the slot. In an exemplary embodiment of the invention, this provides flexibility in wire holding and wire positioning.

(b) Bracket 100 includes no moving parts to assemble (in site or in factory), break, manipulate and/or get caught. This may also improve hygiene.

(c) The size of bracket 100 is comparable (in all three dimensions) to common self-ligating brackets. The buccolingual dimension can be small compared to common self ligating brackets.

(d) A wire can be easily inserted into the labyrinth-like channels and remains trapped and can be removed without any special tools. This may be useful for teeth where wires tend to snap out. Optionally or alternatively, an external elastic element is mounted on the bracket and helps keep the wire in place. In an exemplary embodiment of the invention, when a wire attempts to leave the channel, a substantial part of force applied by the wire, is damped by the retaining elements of the channel. Optionally, this means that additional forces needed (if at all) to maintain the wire in the channel are smaller, for example, less than 50%, 20%, 10%, 5% or intermediate percentages of forces applied by standard ligation elements.

(e) A wire inside the gingival and incisal channels is hidden behind the bracket wings, which can enhance aesthetics during treatment.

(f) Bracket wings are rounded and/or directed in an oblique direction which may assist in ligation using mini modules or class II elastics and/or attaching elastics in various directions. For example, the direction of the elastic traction may vary in different situations, and the oblique direction of the wings supports such these directions.

(g) Bracket 100, as shown is designed to support existing work practices: for example, the familiar edgewise channel using conventional (elastic or metal) ties, which may be used for torque or finishing.

(h) Form matching tooth contour and/or rounded edges to reduce irritation.

Exemplary Wire-Bracket Interactions

FIGS. 2A-2D show exemplary interactions of a wire 200 and bracket 100. It should be noted that multiple wires may be provided simultaneously. Thereafter, FIGS. 3A-3G will show the usage of such in interactions in the context of a multi-tooth treatment.

Figure 2A:
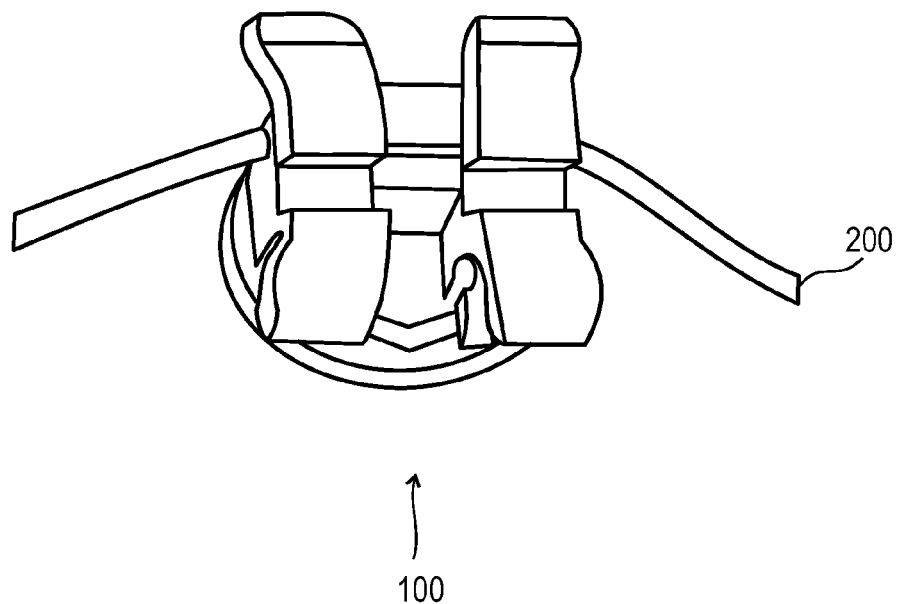
FIG. 2A is a perspective view of the bracket of FIG. 1H, in accordance with exemplary embodiments of the invention, wherein a wire is located in an incisal channel thereof.

FIG. 2A shows wire 200 located in incisal channel 102. In the embodiment shown, the incisal channel is straight and the gingival channel is angulated, however, either or both channels can be straight or angulated and split or not.

In some cases, more rigid wires are used in the non-angulated channel, depending, for example, on one or more of the wire flexibility, angulation and/or wire diameter. More flexible wires are optionally used in any channel and/or pathway, noting that some wire path configurations may be limited to wires of suitable flexibility and/or diameter.

Figure 2B:
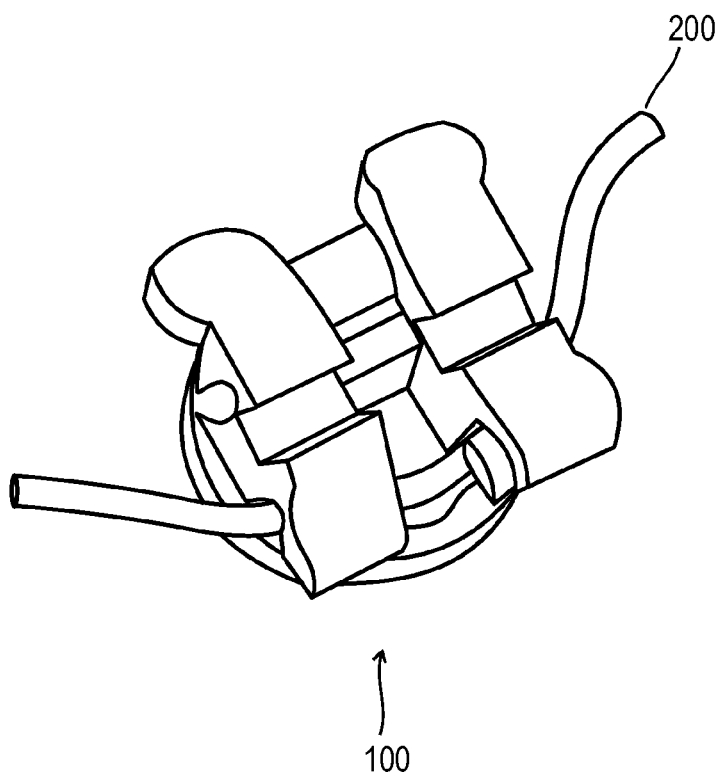
FIG. 2B is a perspective view of the bracket of FIG. 1H, wherein a wire is located in both split angulated channels, according to some embodiments of the invention.

FIG. 2B shows wire 200 located in both split angulated channels, which in this example is the gingival channel 104. It should be noted that wire 200 is optimally maintained in a bent configuration by the angulations of channel 104. Optionally, this provides some friction between wire 200 and bracket 100, depending on the layout of the channel. In other embodiments and/or wires, the wire is not maintained bent and can straighten out in the channel. Depending on the angulation angle, this channel may be restricted to more flexible wires.

Figure 2C:
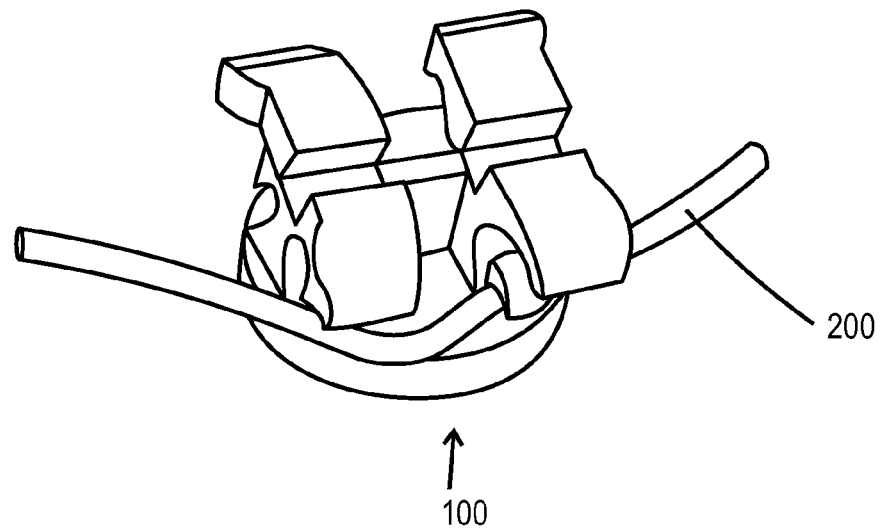
FIG. 2C is a perspective view of the bracket of FIG. 1H, wherein a wire is partly in a gingival channel (angulated channel) and partly in a wire guide, according to some embodiments of the invention.

FIG. 2C shows wire 200 partly in gingival channel (angulated channel) 104 (in section 124 thereof) and part in wire guide 118, which lies outside of section 122. As can be appreciated, this causes a rotation force on bracket 100, which may be used for tipping, depending on the neighboring teeth alignment and bracket attachment.

Figure 2D:
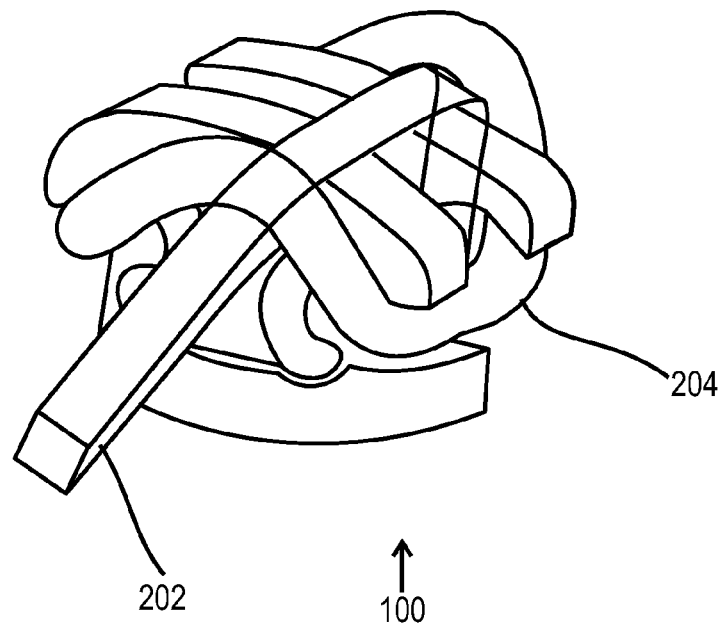
FIG. 2D is a side view of the bracket of FIG. 1H, wherein a square wire is located in a channel therein, according to some embodiments of the invention.

FIG. 2D shows a square wire 202 in channel 106. In some cases, an elastic member 204 is attached to keep wire 202 inside channel 106 or to urge wire 202 into channel 106 if the bracket alignment does not allow inserting thereto.

Optionally or alternatively, elastic element 204 is used to prevent wires from escaping from channels 102 and 104.

Exemplary Teeth Manipulations

FIGS. 3A-3G illustrate exemplary teeth manipulation configurations using a bracket 100 as described above.

Figure 3A:
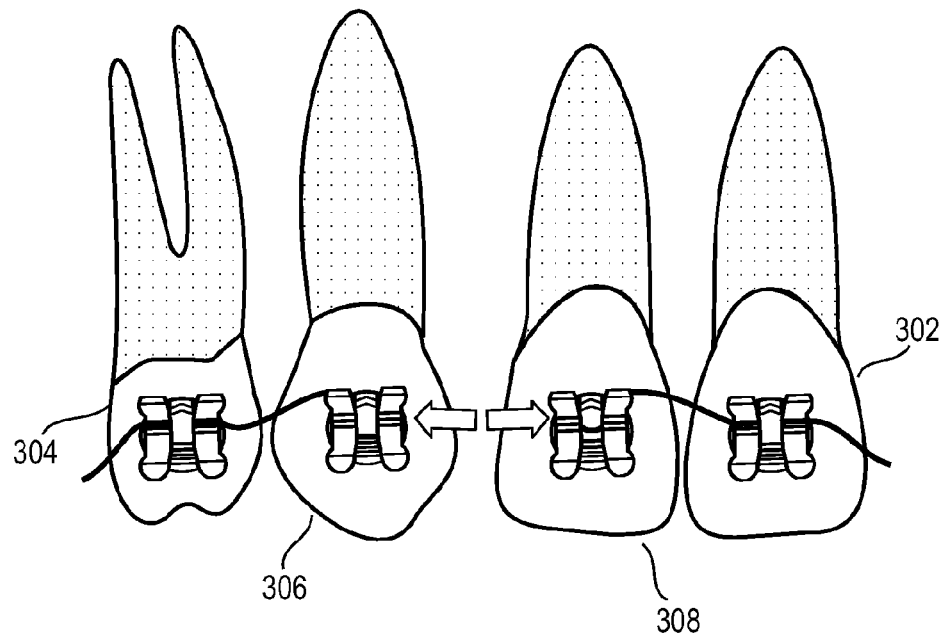
FIG. 3A illustrates force application on teeth using the brackets of FIG. 1H, in accordance with exemplary embodiments of the invention, for opening a space for an implant.

FIG. 3A shows an example of opening a space for an implant by moving the roots of two neighboring teeth (torque).

In this example, gingival angulated channels are used in two outside teeth 302, 304, in both angulated channel portions, so the wire lies passive in the channel without any activation of root movement. Optionally, the activation configuration shown in FIG. 2C is used in two neighboring teeth 306, 308, the mesial angulated channel is engaged on the canine (306), creating a distal root movement, and the distal angulated channel is engaged in the incisor (308), creating a distal root movement. Therefore both roots move apart creating space for the implant insertion. Optionally, one or more springs are provided between teeth 306 and 308, on the wire, to push apart the teeth.

Figure 3B:
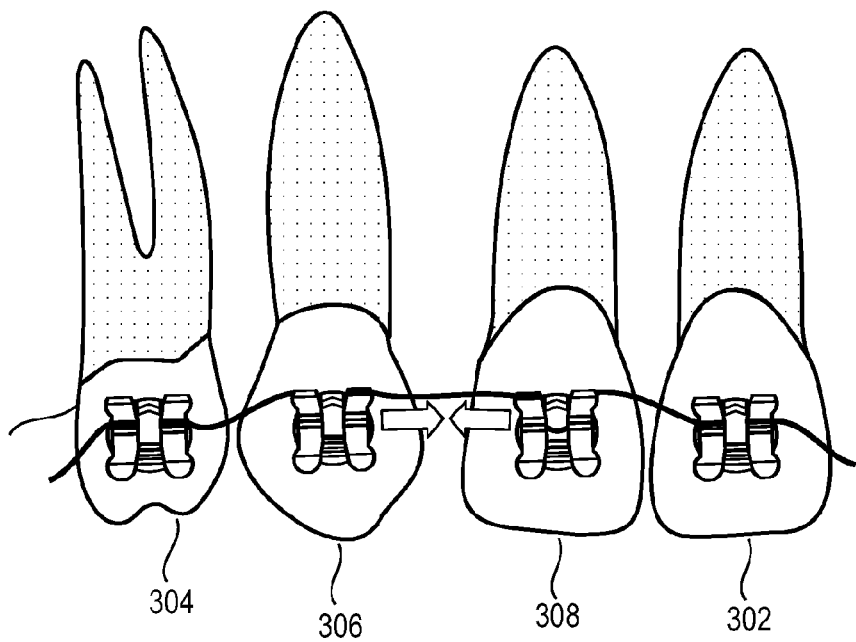
FIG. 3B illustrates force application on teeth using the brackets of FIG. 1H, wherein the roots of teeth are moved towards each other, according to some embodiments of the invention.

FIG. 3B shows an example similar to that of FIG. 3A, where the roots of teeth 306 and 308 are moved towards each other (opposite from FIG. 3A where they are moved away form each other), to close a space. Optionally, one or more springs are provided between teeth 306 and 308 to pull them together, thereby providing bodily movement. Optionally or alternatively, a wire is provided in the incisal channel, to assist in maintaining alignment. Optionally, the wires in the different channels are of different degrees of resilience.

Figure 3C:
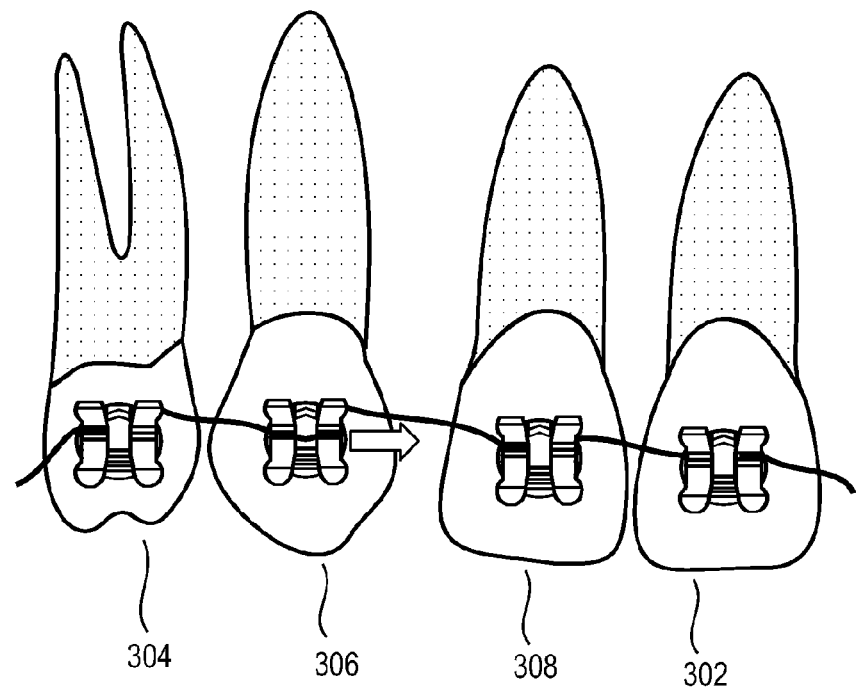
FIG. 3C illustrates an alternative of force application, in which only the root of one tooth is moved mesially, to close a gap, according to some embodiments of the invention.

FIG. 3C shows an alternative to FIG. 3B, in which only the root of tooth 306 is moved mesially, to close a gap. All the teeth have the wire in both angulated channel portions in the gingival channel 104, except for tooth 306 which follows the layout of FIG. 2C. Optionally, the other teeth are tied together, for example, using wires or elastic bands on the brackets to prevent their movement except as a group and thereby substantially anchor them in place.

Figure 3D:
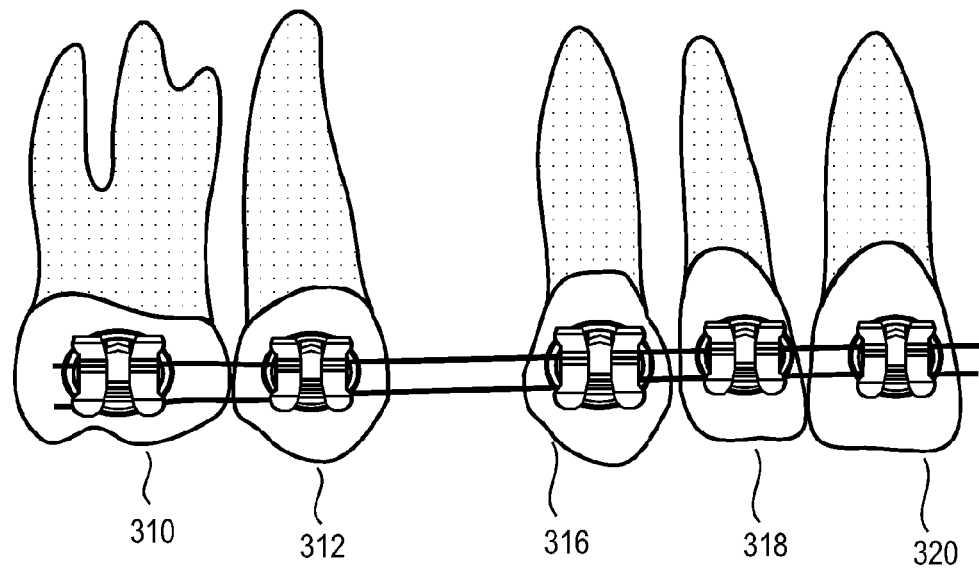
FIG. 3D illustrates the use of multiple wires for translating of teeth, according to some embodiments of the invention.

FIG. 3D shows an example using multiple wires. Wire 200 is in incisal channel 102 and guides translating of teeth 310 and 312. A thick wire 202 is coupled to channel 106 in teeth 316, 318 and 320, 310 and 316. Elastic modules are used for brackets on teeth 316, 318, 320, maintaining the wire in place and not coupled to channel 106 in teeth 310, 312, allowing them to travel along wire 200, without binding and/or without friction. One or more springs or elastics (not shown) are optionally provided to provide a motive force for the translation.

Figure 3E:
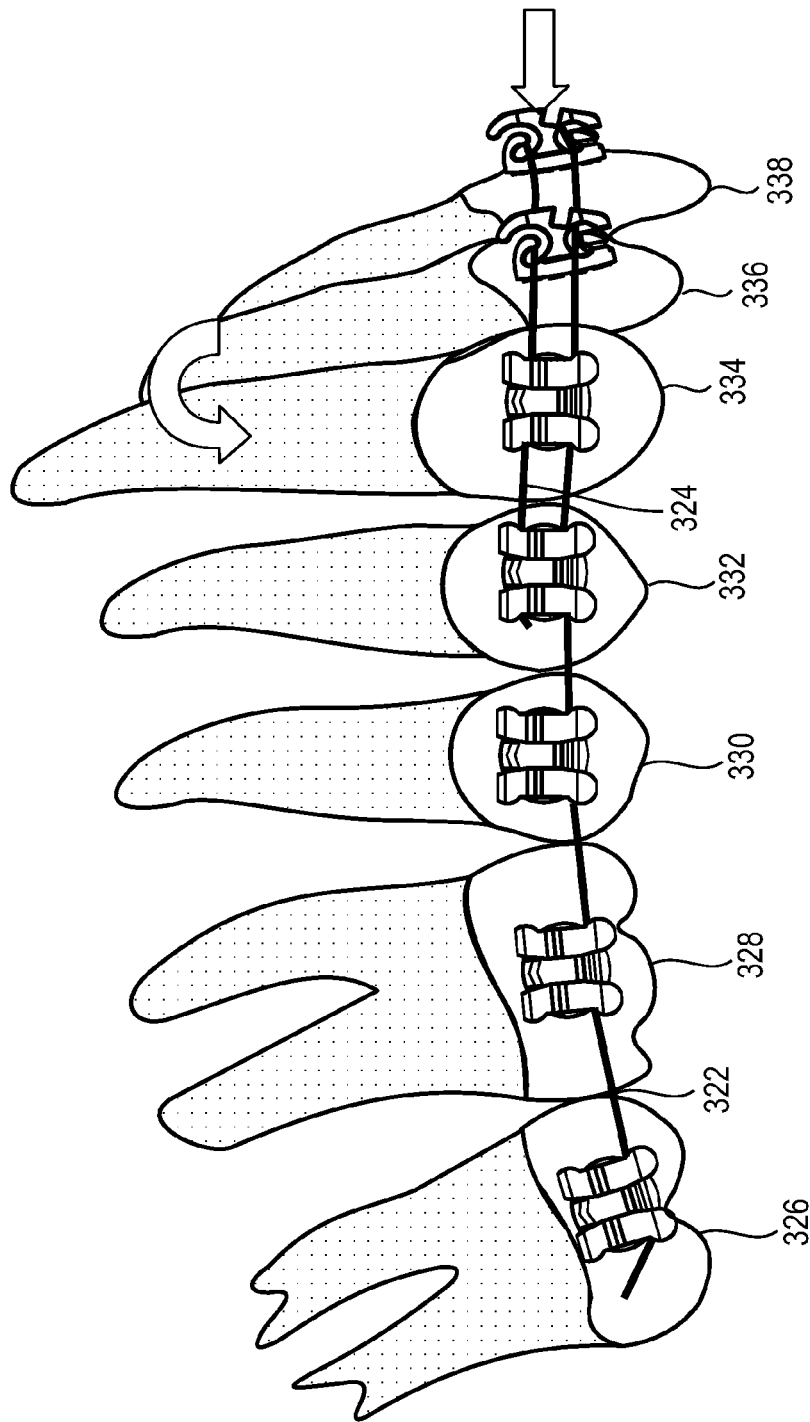
FIG. 3E illustrates the application of lingual root torque for teeth, according to some embodiments of the invention.

FIG. 3E shows an example of lingual root torque for teeth 334, 336, 338, using a stiff wire in the incisal channel and an elastic wire on the gingival channel; an incisal wire 322 lies in incisal channel 102 and maintains the alignment of the teeth (326-338) and a gingival elastic 324 lies in gingival channel 104 of teeth 332-338 and thereby causes lingual root torque on teeth 334, 336 and 338. In tooth 326, the end of the wire is held in place by distortion thereof (e.g., crimping). In tooth 332, the end of the elastic is held in place, optionally by a tie.

Figure 3F:
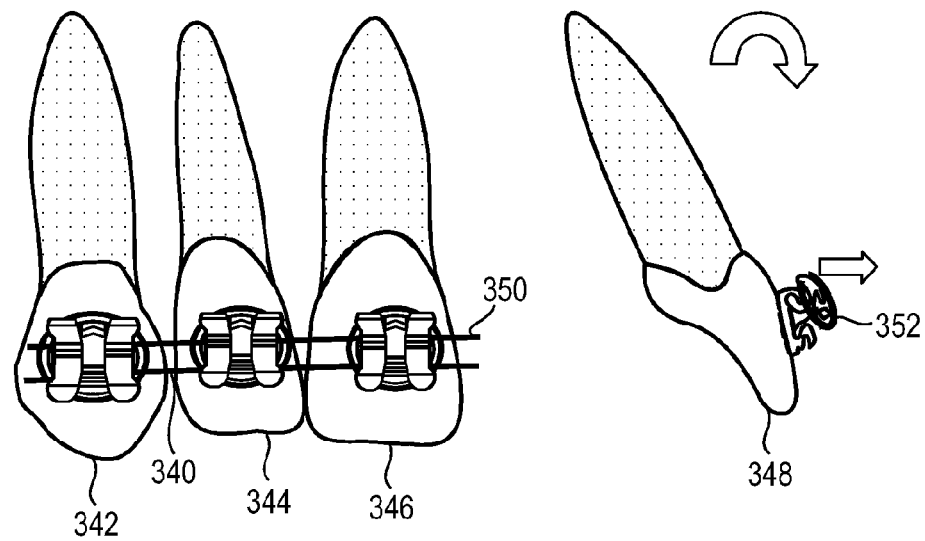
FIG. 3F illustrates the application of labial root torque for a single tooth, according to some embodiments of the invention.

FIG. 3F shows an example of labial root torque for a single tooth, in which a wire 340 in incisal channel 102 maintains teeth 342, 344, 346 and 348 aligned and a rectangular wire 350 is engaged in rectangular channel of teeth 342, 344 and 346, maintaining the torque of these teeth. Wire 350 is not engaged on tooth 348 which needs labial root torque, it is optionally positioned outside the channel, buccal to the channel by performing a step-out bend in the wire. An elastic 352 which is tied from this offset bend to a (or both) gingival tie wing causes labial root torque in tooth 348. The elastic elements may also assist in maintaining wire 340 inside its channel and/or apply some friction to it. In this and other figures, the wires are not shown in their entire length, to reduce clutter in the drawing.

Figure 3G:
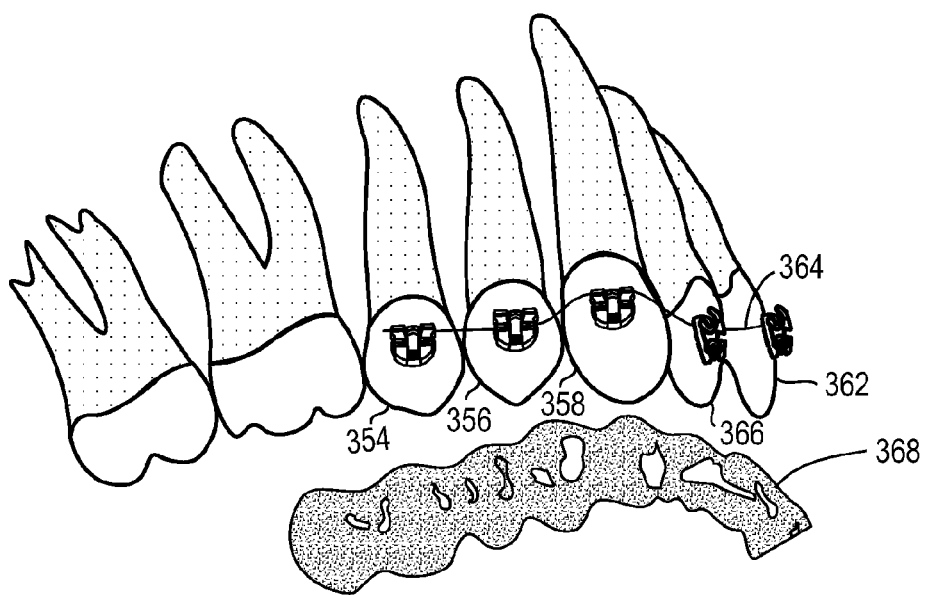
FIG. 3G illustrates active attachment in which a simplified (only one channel, self-ligating) palatal or lingual bracket is used on a plurality of teeth, according to some embodiments of the invention.

FIG. 3G shows active attachment in which a simplified (only one channel, self-ligating) palatal or lingual bracket is used on a plurality of teeth 354-362 and holds a wire 364 for providing active alignment. Optionally or alternatively, these simplified brackets are used together with a clear active plate to assist in creating movements which are difficult for the clear plates, such as intrusion extrusion or rotation (e.g., an Invisiline™ type plate).

In the art, a wire is bonded to the teeth. In an exemplary embodiment of the invention, brackets bonded permanently of the palatal side of the teeth with the wire engaged but not bonded. Optionally, small corrections are possible even during the retention phase.

In an exemplary embodiment of the invention, the location of the wires is selected for more precisely selecting a center of rotation of a force applied by the bracket, for example, for one or more of torquing, angulation, tipping and/or rotating.

In the above examples, the wires used may be rigid or flexible, depending on the desired effect. In general, a rigid wire holds teeth alignment better (and applies greater force), even when the rigid wire is round and in a self-ligating channel (e.g., 102, 104).

Exemplary Procedure

The usage of bracket 100 may be clearer by following the following theoretical case study.
Case Description
Class II open bite case due to under-eruption of upper incisors, with severe crowding in the upper and lower incisors region. X-bite of right lateral incisors, with the root of the upper right lateral incisor palatally and mesially positioned, gingival recession of the lower right lateral incisor with the root buccally positioned. Severe vertical bone loss of the lower left central incisor. Labial impaction of the upper right canine and palatal Impaction of the upper left canine
Treatment Plan
  1. Extraction of two upper first bicuspids to correct crowding and open bite
  2. Surgical exposure of the upper canines
  3. Labial root torque and uprighting of the upper right lateral incisor, Lingual root torque of the upper right canine and labial root torque of the upper left canine.
  4. Extraction of lower left central incisor and closing the space to resolve the crowding by moving the adjacent teeth to the space created
  5. Lingual root torque of the lower right lateral incisor with the gingival recession
Treatment Progress
  1. The patient is referred for extraction of the upper first bicuspids and the lower left central incisor.
  2. Bracket positioning. Brackets are placed on the midpoint of the facial axis of the clinical crown following the principles suggested by Andrews. Brackets are optimally positioned in any case and therefore there would be minimal need for repositioning the brackets after generating an exaggerated movement:
   No overangulation is required in almost any situation (for example the upper right lateral incisor has to undergo significant translation and root movement in the distal direction,) since over-torque and over-angulation can be decided during treatment and performed easily by the bracket. This enables ideal bracket positioning from the beginning of treatment, and ideal finishing without needing to reposition the bracket (to cancel the overcorrection) after the translation or torque has been completed.
   The combination of the 3 channels can give the clinician numerous options to change the torque values compared to prescribed torque that should be built in other bracket system. Torque can be generated individually to any tooth to completely correct its position. Optionally, each bracket may be provided with a different angle of the channels.
   There is no need to choose a bracket with a torque value that will exaggerate the tooth movement required (such as a low torque bracket for a palatally placed upper lateral incisor).
   No additional torque will needed to be placed in the archwire to obtain ideal root position.
  3. Treatment Phases, Archwire Selection and Archwire Sequencing
Phase 1: Alignment with Light Round Wires
   This phase of treatment uses 0.012", 0.013", or 0.014" nickel titanium archwires placed in the gingival angulated channel. The distal angulated channel of the lower left lateral incisor and the lower right incisors will be engaged in order to achieve over angulation and root movement to the lower incisor extraction site. All the other brackets will be engaged straight in the gingival channels. In this way force application is precise to the point where it is needed with minimal side effects typical to the use of a continuous archwire.
   Severely displaced teeth are managed by creating space for the teeth with an open coil spring on the resilient wire in the gingival channel; this can be done with low forces and the coil spring should be no longer than the width of the space plus a bracket width (approximately 3 mm), while controlling the root position by selective use of the mesial or distal angulated channel portion. Since the archwires are free to swivel to mesiodistally and cause "wire pokes" and irritation to the oral mucosa, the wires are optionally stabilized using archwire stops. Stops could be made of flowable composite.
   To stop the archwire swiveling, composite stops are placed either side of a bracket or at either end of an interbracket span, optionally in an unseen area.
   Stops should be placed on a section of the archwire where little movement of the archwire relative to the bracket is expected to occur. Optionally, such locations are selected by providing a wire with less angulation and/or no springs and/or by grouping together teeth to act as anchors and/or by using an orthodontic anchor.

Generally, placement of the stops distal to the cuspids will ensure that the anterior segment will be stabilized Generally, placement of stops at either end of an inter-bracket span can maintain space for an unerupted or prosthetic-implant supported tooth.

The patient is instructed to wear light vertical elastics during sleep hours for extruding the incisors. The elastics are easily tied (e.g., mounted on) to the brackets tie wings.

The aims of this phase of treatment are to:

Align the teeth

Move the roots of the lower right central incisor and left lateral incisor towards the space of the extracted central incisor Level the arches excluding second molars. (Second molars are not engaged by the initial archwire until the second phase of treatment to avoid dislodging the light nickel titanium wires)

Correct rotations

Initiate open bite correction

This phase of treatment normally lasts 10 weeks and the second appointment is after 10 weeks.

Phase 2: Torque Control with Rectangular Wires

This phase of treatment can use two arch wires, one a reuse of the light round arch wire from the previous phase and a rectangular nickel titanium wire for torque control, 0.014× 0.022 or 0.016×0.022 (in inches) depending on the alignment needed.

For this specific case with an impacted canine an additional wire may be used for extruding the palatally impacted canine with a special spring, while other wire(s) maintains teeth alignment. During this stage the patient is referred for surgical exposure of the canines Closed cleats are bonded to the canines during the surgical process. The upper right canine which is labially positioned is lightly pulled to the archwire with elastics, and the upper left canine which is palatally impacted is extruded to the palate using a finger spring made of 0.014 stainless steel wire, which is engaged in the incisal channel.

When the canines appear in the mouth they are bonded with their brackets and engaged to the light resilient archwire, to be pulled to the arch. At this stage the mesial angulated channel of the right lateral incisor can be engaged in order to move the root of this tooth distally.

When the canines reach the arch the rectangular wire is engaged to the canine bracket channel.

The aims of this stage of treatment are to:

Obtain full alignment of the lower arch

Initiate torque control,

Continue open bite correction and arch development

Extrude the right impacted canine to the arch and the left to the palate.

The duration of this phase of treatment depends on the severity of the impaction. Normally it is 20 weeks. Appointment interval is 10 weeks.

Phase 3: Consolidation and Space Closure

The archwires used in this phase are 0.016×0.022 stainless steel together with a 0.014 stainless steel round wire in one of the self-ligating channels.

Spaces are closed with chain elastics and Class II elastics. The second bicuspid brackets can be bypassed by the chain elastic in order to close the spaces with reduced friction.

If lingual root torque is needed for the lower right lateral incisor, the round stainless steel wire is engaged in the gingival spiral cannel, the rectangular wire is added an offset bend, and an elastic is tied from the offset bend to the incisal tie wing to torque the root lingually. If labial root torque is needed to the upper right lateral incisor or to the upper left canine, the incisal channel will be engaged with the round stainless steel wire, and the torquing elastics will be tied from the gingival tie wing to the offset of the rectangular wire. Optionally or alternatively, the middle channel is used with the prescribed torque. In this way torque is very effective and applied specifically to the individual tooth which needs it, without side effects on the adjacent teeth. Vertical elastics can be continued as needed, Class II elastics can be also used from the tie wings as needed.

The aims of this phase of treatment are to:

Maintain the archform developed in the first two phases

Finish torque control,

Consolidate posterior space

Completely correct anteroposterior, buccolingual and vertical relationships.

This phase of treatment lasts about 10 weeks

Phase 4: Finishing and Detailing

The round stainless steel archwires may be continued in this phase with some detailed adjustments to individual teeth as required.

Additional Theoretical Case Studies

Two additional theoretical case studies are presented.

1. Class II, Division II, increased over-bite, extensive crowding
   a. Round resilient wire (0.014" Ni—Ti) gingival channel from teeth 16-26 and 36-46 for 3-4 months (2 visits).
   b. Additional rectangular wire (TMA 0.016"×0.022"), is places in buccal channel for Torque control between teeth 13-23 for 3-4 months; The combination of the 2 wires enable frictionless alignment in all segments with Torque control on the same time in the anterior segment.
   c. Class II elastics are used to correct the intermaxillary relations between the upper and lower jaws. Round wires (0.014 SS) are placed in upper and lower jaws together with rectangular wire (SS 0.016"×0.022") in upper anterior segments. This combination will enable the elastics to work more efficiently with fewer side effects. 3-4 months.
   d. Finishing stage. 3-4 months. Wire(s) can be sectioned and combined in all 3 channels to eliminate side effects and to prescribe different forces to individual or groups of teeth 2. Class I, increased Over-Jet, crowding. 4 premolars are extracted.
   a. Round resilient wire (0.014" Ni—Ti) in gingival channel from teeth 16-26 and 36-46 for 3-4 months (2 visits).
   b. The wire in the gingival channel is replaced to S.S 0.014" and additional wire (0.014" Ni—Ti) is placed in the incisal angulated channel. In the teeth where uprighting of the root is needed (especially near the extraction sites) the wire is activated (e.g., engaged in the angulated channel); in all other sites it is placed in a way that it will add more control to the teeth movement. Optionally, the wire is coupled to the other teeth in a straight channel or using two angulated portions of a bi-angulated slot, which may add anchorage and/or balance.
   c. Space closure can be done using two round wires (in incisal and gingival channels).
   d. Additional rectangular wire can be added to ensure the torque control and integrity of the arch during space closure.
   e. If torque is needed in the front segment and sliding in the back a rectangular wire can be engaged in the central channel in addition to the round wire in the gingival channel. The rectangular wire can be ligated to the front teeth with elastic or metal ligatures and will be placed freely (or ligated) in the posterior segment for frictionless sliding movements. Optionally or alternatively, the round wire holds the teeth aligned where the rectangular wire is not attached.

f. It is expected that treatment time will be definitely reduced by 20-40% due to the ability to isolate the desired movement and choose the best wires combinations in all 3 channels for every tooth or group of teeth.

Exemplary Effects of Using Exemplary Bracket

In an exemplary embodiment of the invention, the treatment plan changes due to the use of a bracket in accordance with some exemplary embodiments of the invention. One change is due to different wire channels, guides having different specifications and indications and several combinations being possible. Existing treatment protocol is based brackets with one slot, typically self ligating which is limited to certain protocols: Alignment with round resilient wires and only after the alignment is completed, rectangular wires can be used. Ligation of theses wires in self ligating slot could be difficult if the alignment was not perfectly completed and therefore treatment time is prolonged. As shown above, multiple correction types can be applied simultaneously and selectively to individual teeth. In addition, anchorage can be planned differently than currently and overcorrection can be done with the additional angulated channel. For example, where strong anchorage is desired, maximal control will be provided (e.g., using all three channels, or more if more than three parallel channels are provided), while in other places where movement is desired, resilient wires and maximum sliding effect are selected for. Optionally, three-dimensional control is enhanced by the different locations of the channels: Incisal, middle and gingival on the vertical dimension of the tooth and buccal and palatal/lingual side of the bracket in the horizontal aspect of the bracket. Skilled usage of these factors can give the clinician better 3 dimensional control and a more efficient treatment plan.

In an exemplary embodiment of the invention, time per visit is shortened, due, for example, to easy of mounting wires in channels, for example, reduced by 20%, 30% or more. Optionally or alternatively, treatment time is reduced, for example, by one or more of simultaneous correction types on different teeth, greater forces with more precise control and lack of need to reposition brackets.

In an exemplary embodiment of the invention, fewer "first aid" visits will be needed. First, there are no moving parts to break. Second, if forces are applied more precisely (e.g., using a combination of round wires, rather than a thick rectangular wire), bracket is under less strain. Third, improved force control may prevent some or all (e.g., at least 50%, 70% or more) undesired teeth movements. Optionally, "first aid" visits are reduced at least 20%, 30%, 40% or more In an exemplary embodiment of the invention, number of adjustments is reduced. For example, no reactivation is needed if forces are planned to act in all possible channels and vectors, possibly saving 20-30% of the treatment time and/or of the chair time. Optionally, this may reduce costs by reducing the need to replace wires, add module sand/or replace (or custom design) brackets.

Labyrinth-Like Bracket Variants.

Figure 4A:
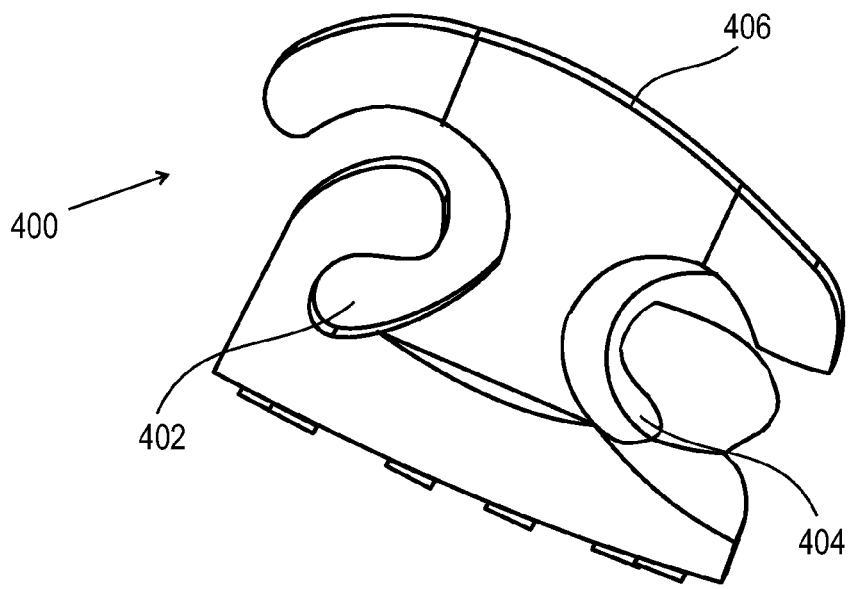
FIG. 4A illustrates a bracket with a reduced number of wire channels, in accordance with an alternative embodiment of the invention, according to some embodiments of the invention.

FIG. 4A shows a bracket 400, in accordance with an exemplary embodiment of the invention, with only labyrinth-like channels 402 and 404 and no edgewise center standard channel. Optionally, a depression is formed as a wire guide at a point 406 between the channels to assist in holding a central wire, if used. This design may allow the thickness and/or height of the bracket to be reduced as no material for supporting the central channel is needed.

Figure 4B:
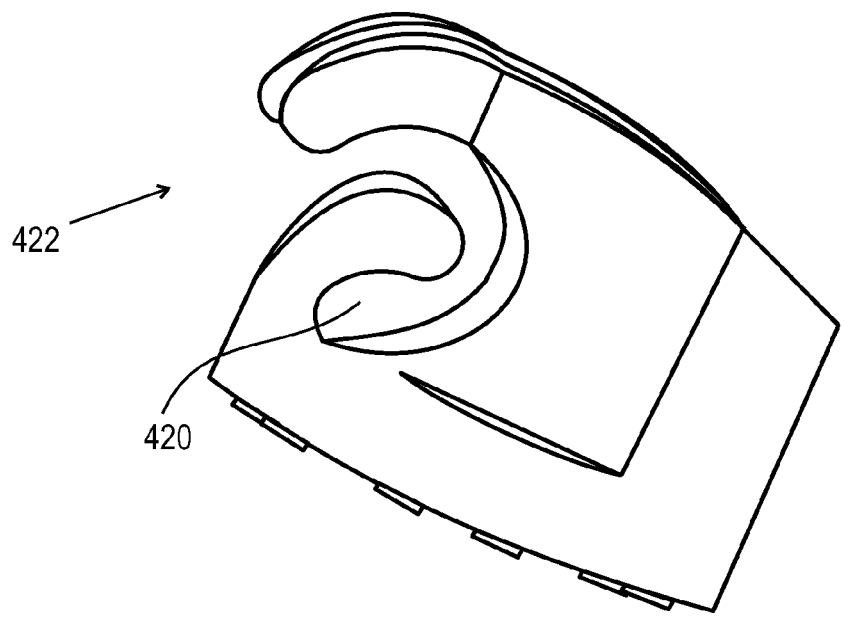
FIG. 4B illustrates a single slotted bracket including an incisal channel (or a gingival channel), according to some embodiments of the invention.

FIG. 4B shows a single slotted bracket 420 including on an incisal channel 422 (or a gingival channel). Optionally, the channel is split, as described with reference to FIG. 1, for example.

Figure 4C:
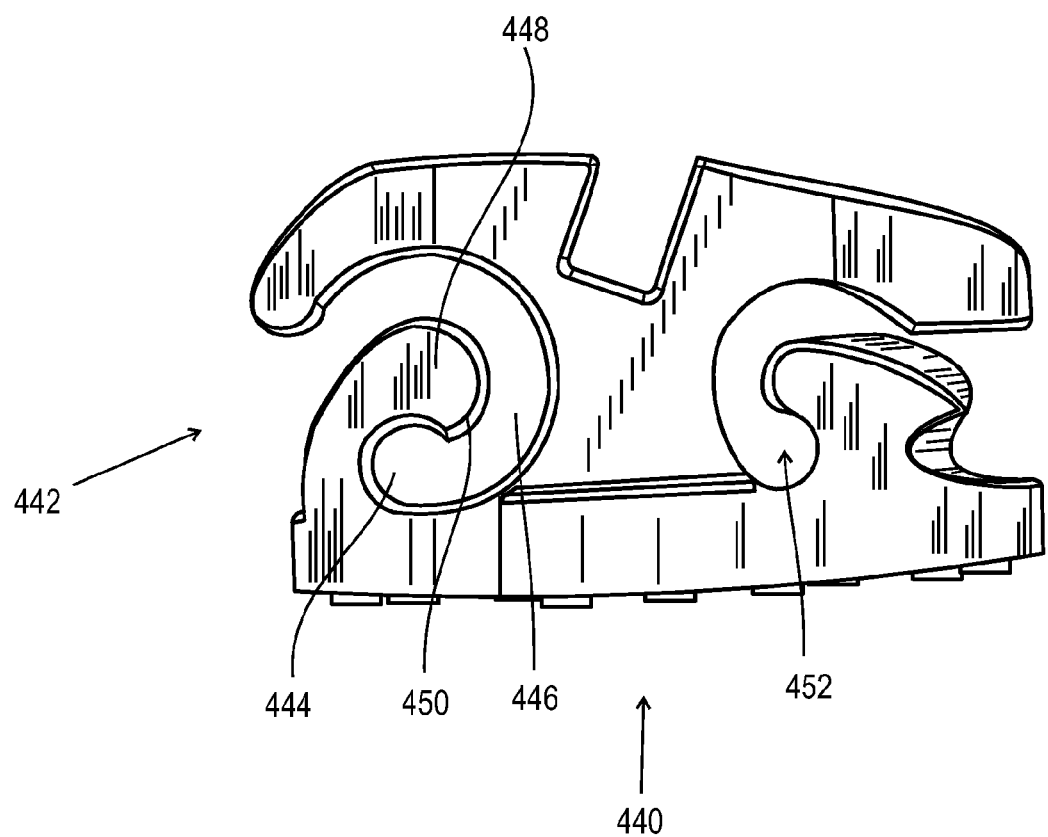
FIG. 4C shows a variant, in accordance with an exemplary embodiment of the invention, of the bracket of FIG. 1.

FIG. 4C shows a bracket 440 which is a variant of the bracket shown in FIG. 1, with respect to its labyrinth-like elements. A gingival channel 442 includes a working area 444 which is less open than in FIG. 1. Rather a passage way 446 and a spiral knob 448 define a spiral with a projection 450 that resists wire removal from working area 444, possibly by being tighter at its end near working area 444. In general, the spiral of labyrinth-like channel 442 has a greater angular length (the accumulated angle traversed when travelling along the passageway) and/or includes a smaller angular opening from working area 444 to passageway 446 (angle measured from center of working area 444). Optionally or alternatively, working area 444 is made more symmetrically circular. Optionally or alternatively, an incisal channel 452 has the same modifications. Optionally, projection 450 acts as a cup or cusp so that movement of the wire along the wall of the working area is not compatible with movement outside of the working area and into the passageway (while it may be in FIG. 1), at least not without an abrupt change in wire direction.

Lingual Bracket

Figure 5:
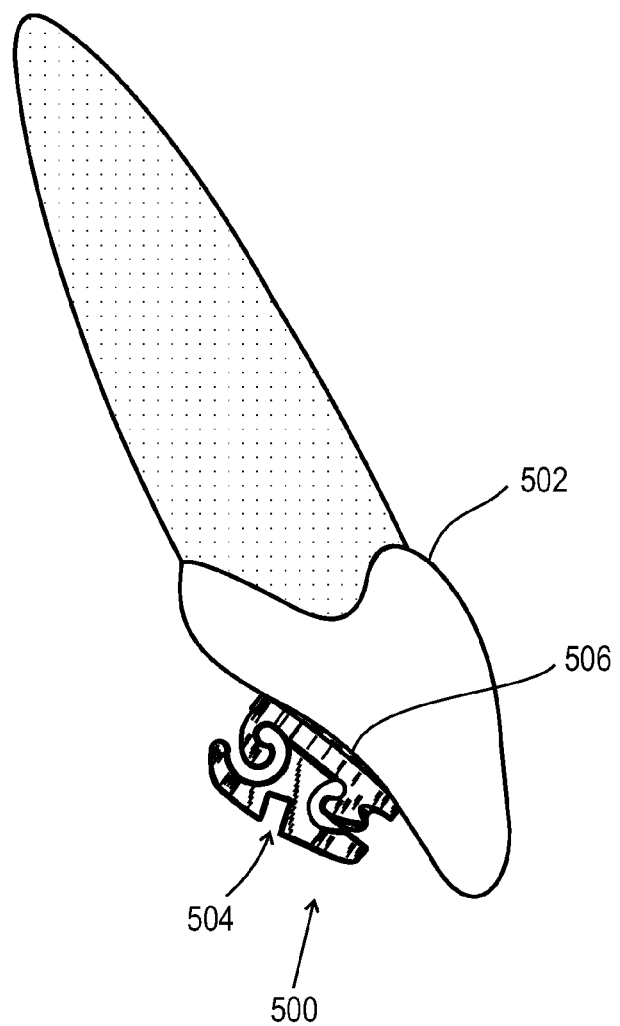
FIG. 5 illustrates a palatal bracket variant, in accordance with an exemplary embodiment of the invention.

FIG. 5 shows a lingual bracket 500 mounted on a tooth 502, showing exemplary possible variations for such a bracket, for example, a different central channel 504 angle and/or a different shape of a base 506 (e.g., convex rather than concave, to match tooth shape.

In an exemplary embodiment of the invention, the bracket of FIG. 5 may allow forces to be applied closer to the center of resistance (CR) of a tooth. This may be useful for applying some forces and/or useful for avoiding other forces. In an exemplary embodiment of the invention, the bracket is made small to avoid tongue irritation and/or reduce chance of accidental peeling. In some cases, the plurality of channels assist with the wire access problem that is generally more on the palatal side, by allowing the choice of a convenient channel.

General Variants

In an exemplary embodiment of the invention, the bracket includes a slot in the incisal channel, perpendicular to the incisal channel. Optionally or alternatively, the incisal channel is angulated (e.g., set up so a wire placed therein will lie at an angle), optionally using different angles from the gingival slot. Optionally or alternatively, the angles on either side of the bracket are different. Optionally or alternatively, the bracket is otherwise made asymmetric. For example, the channel parts (e.g., of a gingival channel) are not equal in length. Optionally or alternatively, the channel is not generally parallel to the base surface of the bracket and/or closure plane of the mouth. Optionally or alternatively, the tiewings on a same side of a bracket are different. Optionally or alternatively, three ligated slots are provided, using methods of the art (e.g., ligatures and elastic modules, such as on the tiewings), rather than wire retaining mechanisms as described herein.

In an exemplary embodiment of the invention, at least one of the labyrinths is stepwise or includes flat sections in the passageway. For example, the labyrinths may be formed only of sections at right angles to each other.

In an exemplary embodiment of the invention, at least one of the labyrinths is sized and shaped to hold a rectangular or other non-round wire.

Distortion Based Wire Retaining Mechanism

Figure 6A:
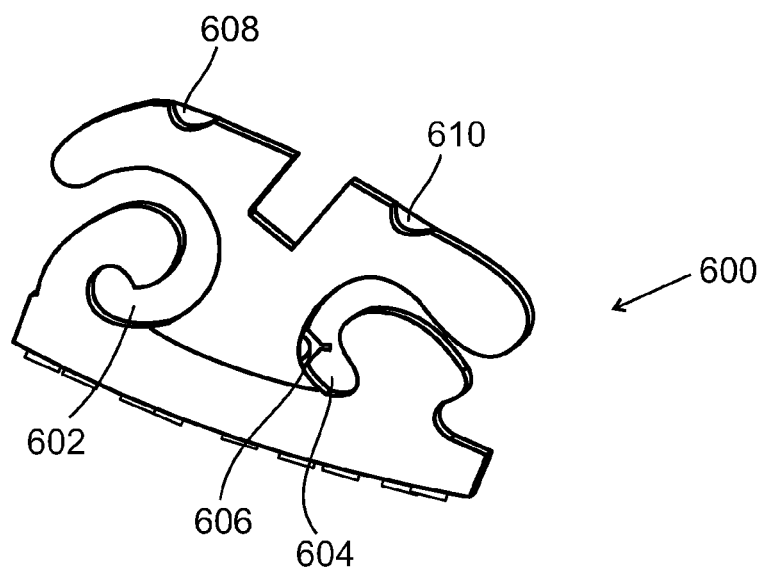
FIG. 6A illustrates a bracket including a distortion based wire holding mechanism and also illustrating upper (buccal) channels for wire guiding and force application, in accordance with an exemplary embodiment of the invention.
Figure 6B:
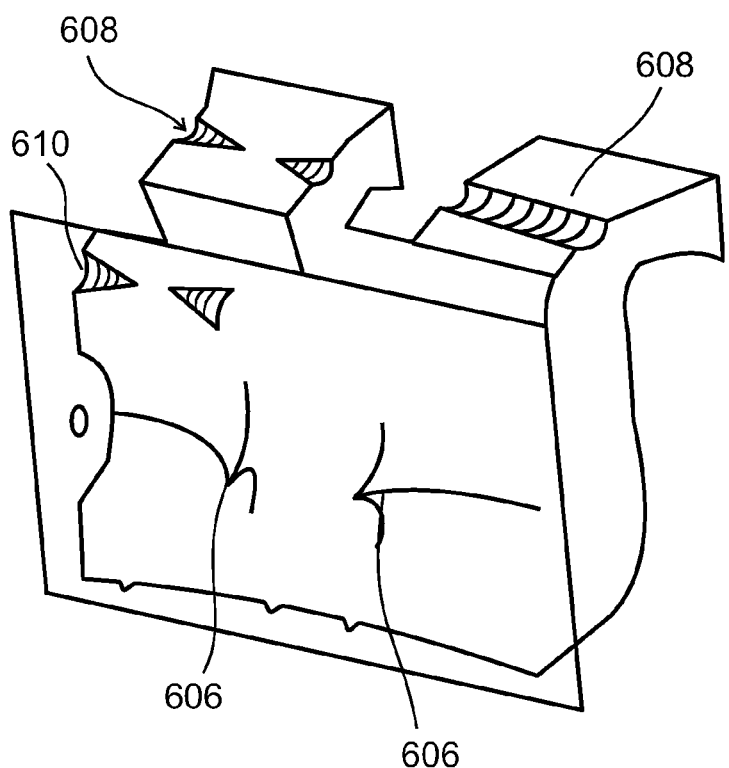
FIG. 6B is a cross-sectional view of the bracket of FIG. 6A, according to some embodiments of the invention.
Figure 6C:
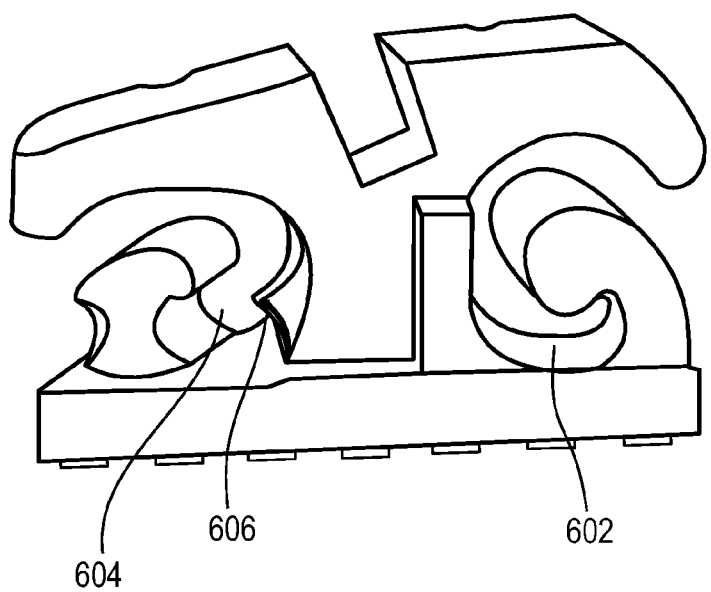
FIG. 6C is a different cross-sectional view of the bracket of FIG. 6A, according to some embodiments of the invention.

FIGS. 6A-6C show a bracket 600 with a distortion based wire retaining mechanism. In bracket 600, this mechanism is used to enhance the retention ability of the labyrinth-like wire retainer. As shown in further figures below, a distortion-based wire retainer may be used instead of a labyrinth-based wire retainer.

Specifically, in bracket 600, an incisal channel 602 and a gingival channel 604 are shown. In gingival channel 604, a projection 606 require a wire to be distorted (e.g., bent) to pass by the projection. A cross-sectional side view can be seen in FIG. 6B and a different cross-sectional side view can be seen in FIG. 6C. As can be seen in FIG. 6C, the projection cooperates with the shape of the channel and passageway so that at every part the channel and passage way are wide enough to pass a wire of the desired diameter. As seen in FIG. 6B, one projection is provided on either side of a slot splitting channel 604. In some embodiments, each projection is sufficient on its own to hold a wire. In other embodiments, both projections are needed. Optionally or alternatively, a projection is sufficient if the wire is then bent in a certain manner along wire guides formed in the bracket.

In an exemplary embodiment of the invention, the side of projection 606 facing a wire insertion direction is curved to guide the wire to correctly distort. Optionally or alternatively, the side facing wire removal is formed to not assist or impede such removal. For example, the removal face of projection 606 (if followed by the wire) may guide an additional distortion of the wire (which may be difficult and/or require more force) and/or may be curved inwards, acting as a cup to hold the wire.

Also shown in FIGS. 6A and 6B, one or more wire guides 608 and 610 may be provided on a buccal face of the bracket, guiding a wire that passes through a part of one of channels 602 and 604. Optionally, one or both of two designs are used. A design 608' has a wire guide along the entire buccal face of an element. A design 608 has the guide formed as recesses in the leading and/or trialing sides of such a face, so as to guide a wire as it curves onto or off of the face.

Figure 6D:
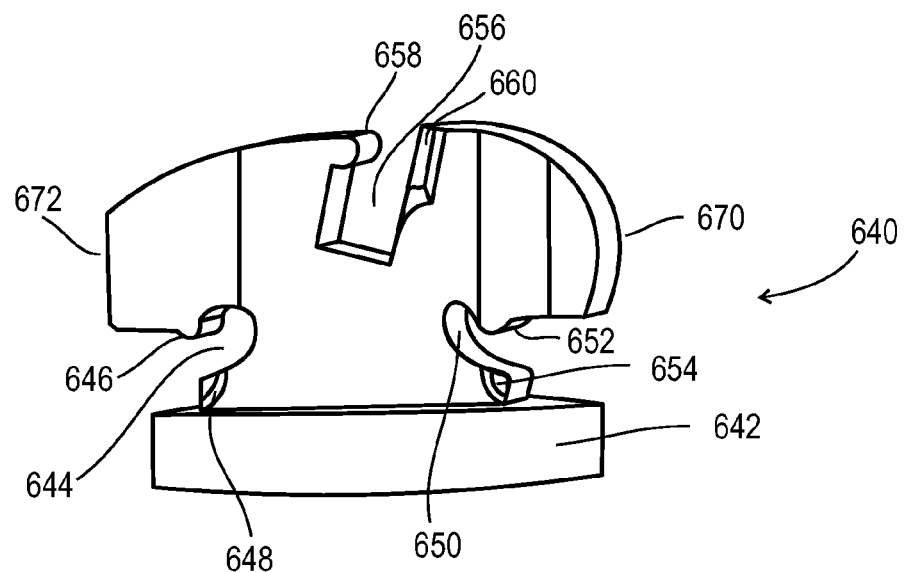
FIG. 6D shows an alternative bracket including a distortion based wire holding mechanism, in accordance with an exemplary embodiment of the invention.

FIG. 6D shows an alternative bracket 640 in which a incisal channel 646 and a gingival channel 650 both include only a distortion based mechanism and not a labyrinth-like mechanism. Optionally, tiewings 672 and 670 are provided, even though they do not serve a wire retaining purpose.

Referring to channel 644, a protrusion 646 and a matching recess 648 formed at extreme ends of the channel, require a wire to be distorted at both ends of the channel so as to fit in. It is expected that such distortion is unlikely to occur randomly. A similar set of projection 652 and recess 654 is shown for channel 650.

In an exemplary embodiment of the invention, a similar mechanism is used in a straightedge channel 656 (a projection 658 and a recess 660). Generally, for more rigid wire, smaller distortions are possible and the projections are appropriately smaller.

Figure 6E:
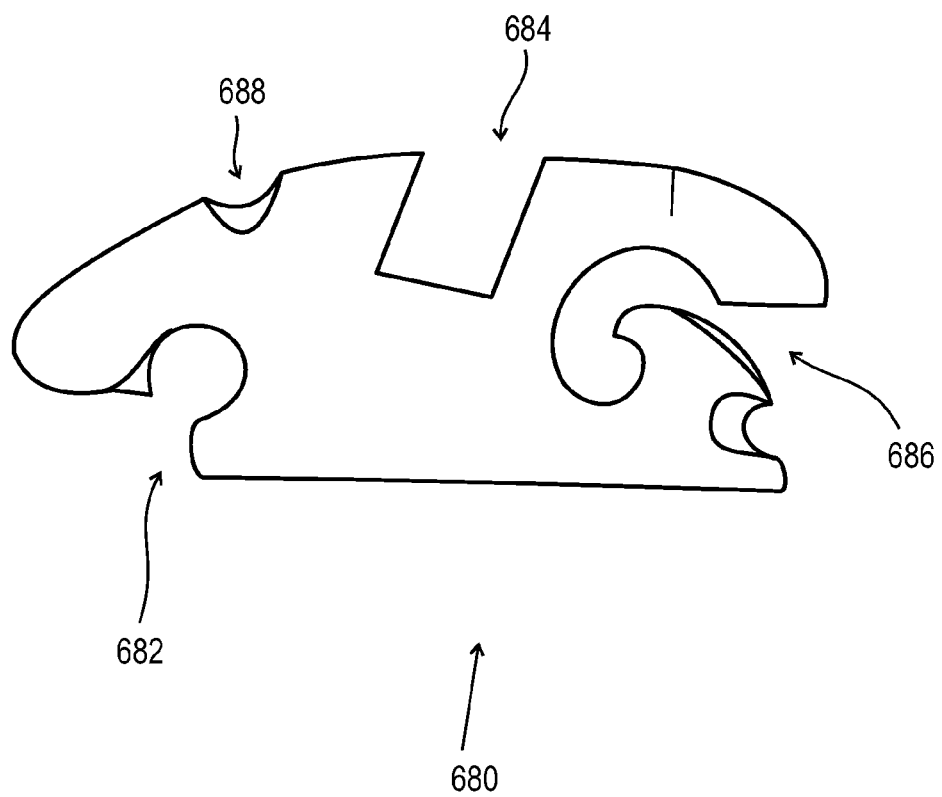
FIG. 6E shows an alternative bracket including both a distortion based wire holding mechanism and a labyrinth-based wire holding mechanism, in accordance with an exemplary embodiment of the invention.

FIG. 6E shows an alternative bracket 680 including both a distortion based wire holding mechanism for a channel 682 and a labyrinth-based wire holding mechanism for a channel 686, in accordance with an exemplary embodiment of the invention. Optionally, a standard channel 684 is provided. Optionally or alternatively, a wire guide 688 is provided.

Reduced Thickness Brackets

FIGS. 7A-7D illustrate brackets with a lesser buccal dimension (e.g., 50% less than of FIG. 1), in accordance with an exemplary embodiment of the invention.

Figure 7A:
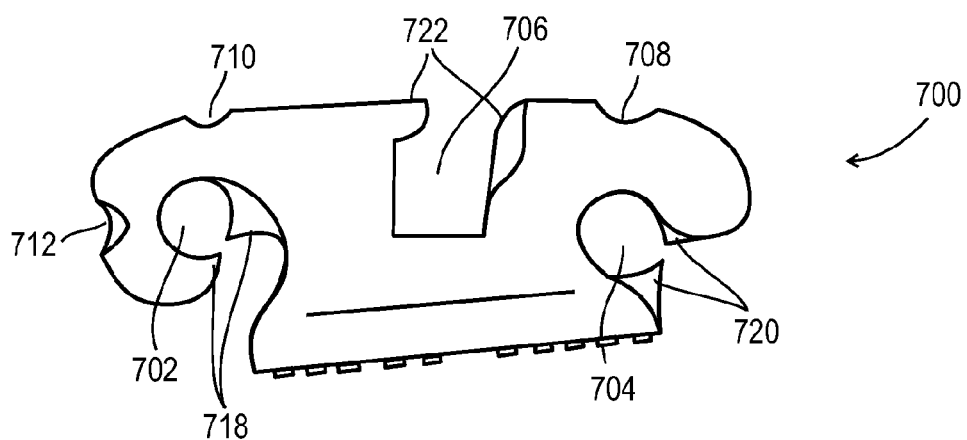
FIG. 7A illustrates a bracket with a lesser buccal dimension, in accordance with an exemplary embodiment of the invention.

Referring specifically to FIG. 7A, a reduced buccal dimension is achieved because a standard channel 706 (with an optional distortion based wire retaining mechanism 722), is placed between gingival channel 704 (using a retainer mechanism 718) and incisal channel 702 (using a retainer mechanism 720). Due to lack of labyrinths, the length of the bracket can remain the same or smaller as bracket 100, without the channels interfering with each other. In an alternative embodiment of FIG. 1, channels 102 and 104 may be further apart, so that channel 106 can be closer to the tooth. Also shown are exemplary wire guides, for example, an incisal wire guide 712, and buccal wire guides 710 and 708, which may guide wires held in parts of the channels, thereby providing rotation and/or torque and/or tipping forces.

Referring specifically to incisal channel 702, it is noted that the opening of channel 702 is towards the body of bracket 700, which may serve as a partial labyrinth. Optionally, such a form guides a wire during insertion and no such guiding is provided for random movements.

Figure 7B:
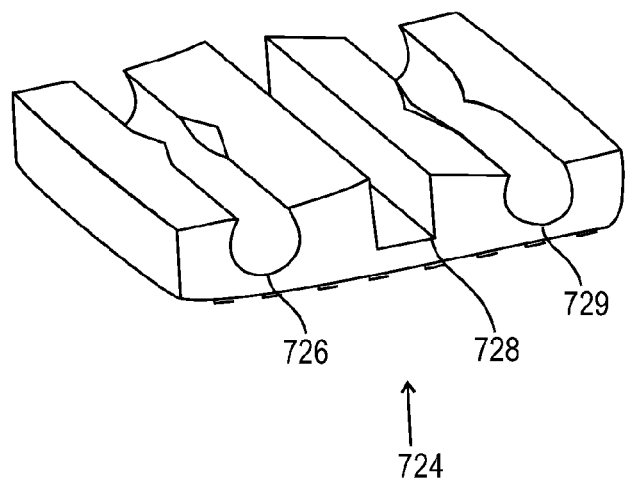
FIG. 7B illustrates a bracket having three channels, wherein two of the channels are distortion based, in accordance with an alternative embodiment.

FIG. 7B shows a bracket 724 having three channels (726, 729 being distortion based and a standard 728), all of which open buccally. Optionally, fewer channels are used.

Figure 7C:
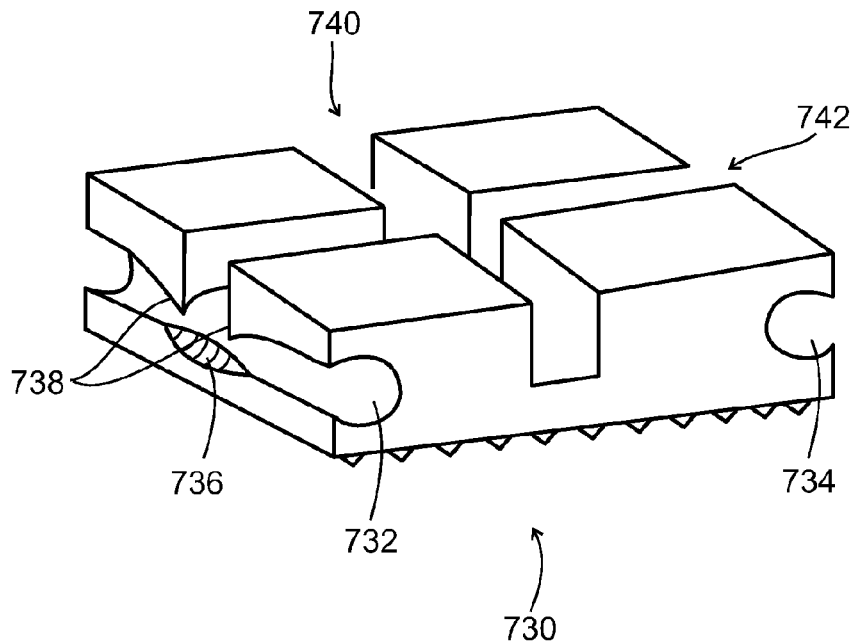
FIG. 7C illustrates an alternative bracket having an incisal channel and a gingival channel, in accordance with a further embodiment.

Referring to FIG. 7C, an alternative bracket 730 is shown, in which a flat body is provided with an incisal channel 734 (wire retainer not shown) and a gingival channel 732 (using one or more protrusions 738 and a recess 736 as a wire retaining mechanism). Optionally, a slot 740 acts as a center channel. Optionally or alternatively, a slot 742 is provided which bisects one or both of channels 732 and 734. In an exemplary embodiment of the invention, slots 740 and 742 serve as wire pathways for applying rotational forces to the bracket. In this and other designs, edges are optionally rounded to reduce irritation to tissue and/or to better hold wires (e.g., at curves). It is noted that the thickness of bracket 730 can be minimal, for example, on the order of 1.3-2 times a design wire thickness.

In this and other embodiments, optionally, the channels are not originally assigned to be incisal or gingival, providing another degree of flexibility.

Figure 7D:
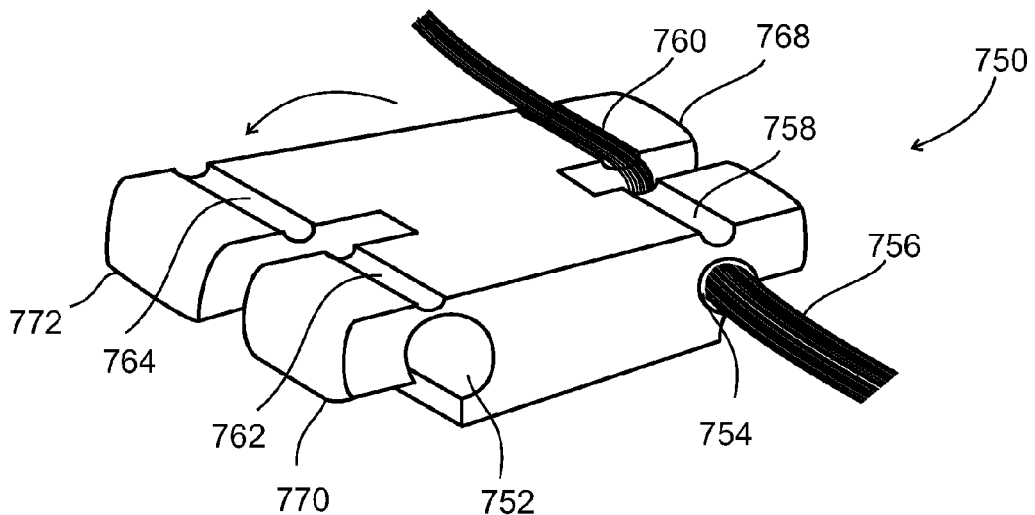
FIG. 7D illustrates an alternative flat bracket, wherein the bracket has no central slot, according to some embodiments of the invention.

Referring to FIG. 7D, an alternative flat bracket 750 is shown, which bracket lacks a central slot (but such a slot may be provided). Two channels 752 and 754 with retaining mechanism as described above are provided. Optionally, tiewings 770, 772 768 and 766 are provided which may be used for holding elastic modules and/or hiding a wire. As shown, a wire 756 travels in channel 754 in a section underlying tiewing 766 (which has an outside wire guide 758 formed therein) and then passes buccally through a slot between tiewings 766 and 768 to be guided by a wire guide 760 formed in tiewing 768. Optionally or alternatively, to forming on tiewings, wire guides may be formed on other buccal parts of the bracket. Additional optional wire guides 762 and 764, formed adjacent channel 752 are shown as well.

In an exemplary embodiment of the invention, such a wire pathway is used to rotate a tooth around its axis.

Optionally (in this and other brackets), the spacing between the tiewings and the teeth are selected to match the expected wire thickness to be used. Optionally, the direction of opening of the various slots is selected to match the ease of inserting such wires without interference by body parts.

Exemplary Distortion Based Wire Retainers

FIGS. 8A-8I illustrate distortion based wire holding channels, for square wire and/or rounded wires, in accordance with an exemplary embodiment of the invention. Each of the embodiments shown may be useful for different wire types, force applications and/or expected wire release forces.

Figure 8A:
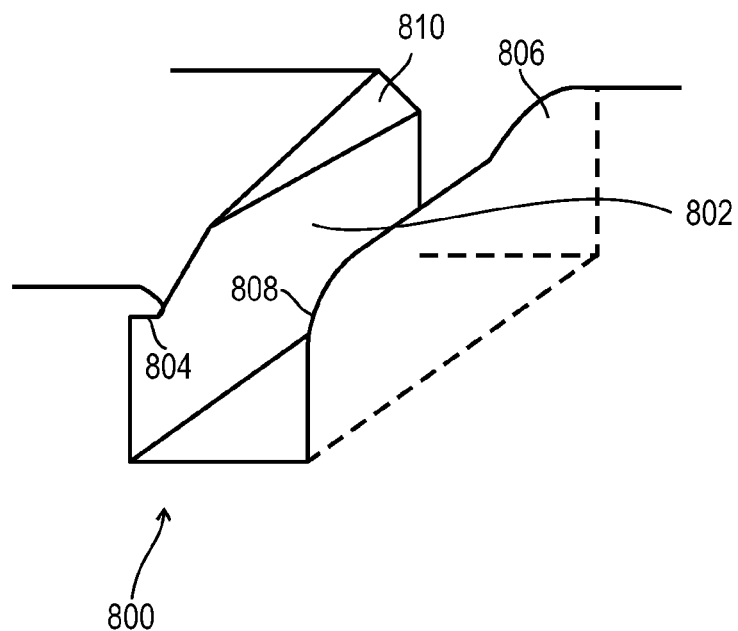
FIG. 8A illustrates a distortion based wire holding channel, in accordance with an exemplary embodiment of the invention.

FIG. 8A shows a wire retainer 800 for a wire, for example square, including a channel 802 and opposite protrusion-recess pairs (804-808 and 806-810) on opposite sides of the channel, or at least displaced apart. To insert a wire into channel 802, the wire should be distorted at both ends thereof matching protrusions 806 and 804. Also as shown an inner face of protrusion 804 is flat, to resist inadvertent exiting of the wire.

Figure 8B:
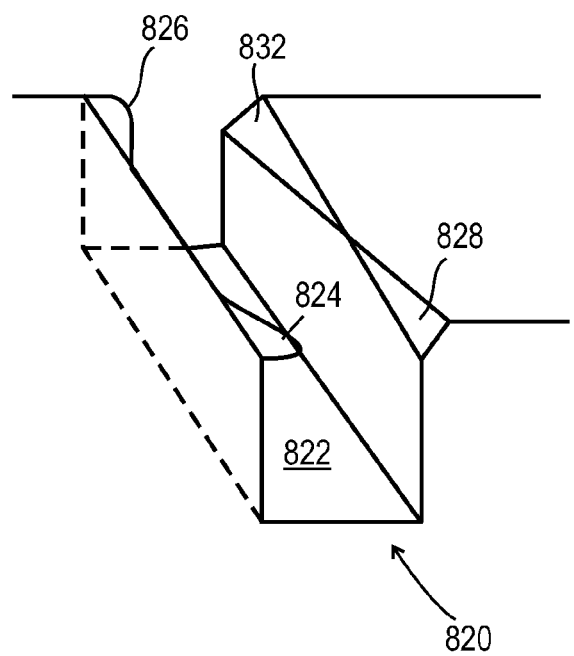
FIG. 8B illustrates an alternative wire retainer for a channel, wherein the channel has protrusions which face in a same direction, according to some embodiments of the invention.

FIG. 8B shows an alternative wire retainer 820 for a channel 822, in which channel 822 has protrusions 824 and 826 which both face in a same direction (optionally each has a matching recess 828 and 830).

Requiring two separate distortions may make it less likely that a wire will pop out. Optionally, a recess is formed in the side wall of channel 822 (or 802). Such a recess can guide distortion of the wire so that if any such distortion occurs is it not likely to be compatible with leaving the channel. Optionally or alternatively, an additional recess is formed underneath an entryway recess, and deeper than the entryway recess, so that if the wire distorts, it will tend to over distort, and will be captured by the additional recess and not release.

Figure 8C:
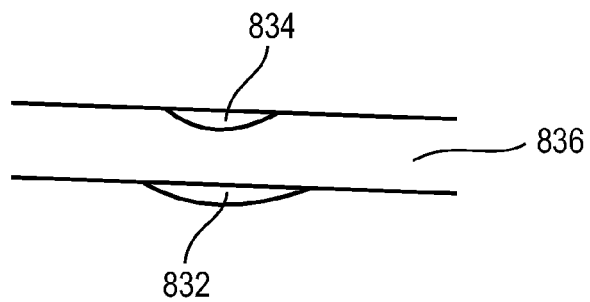
FIG. 8C illustrates a mechanism for a channel 836 (top view), in which a single curved protrusion and matching recess are formed in a center of the channel, according to some embodiments of the invention.

FIG. 8C shows a mechanism for a channel 836 (top view), in which a single curved protrusion 834 and matching recess 832 are formed in a center of the channel (or closer to the ends).

Figure 8D:
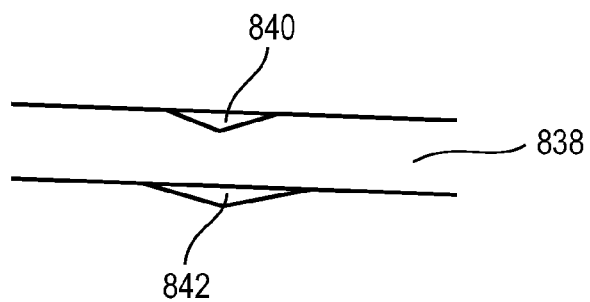
FIG. 8D illustrates a variant of the mechanism of FIG. 8C. according to some embodiments of the invention.

FIG. 8D shows a variant of FIG. 8C for a channel 838, in which a protrusion 840 and/or a recess 842 are angled, rather than curved as in FIG. 8C.

Figure 8E:
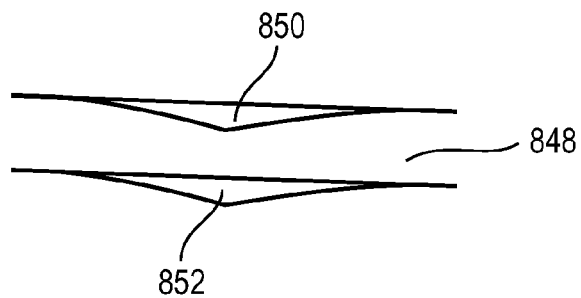
FIG. 8E shows a further variant of the mechanism of FIG. 8C. in which a protrusion and/or a recess extends over a considerable percentage of the length of a channel, according to some embodiments of the invention.

FIG. 8E shows a variant for a channel 848 in which a protrusion 850 and/or a recess 852 extend over a considerable percentage (possibly all) of the length of channel 848. The extent in various embodiments may be, for example, 10%, 25%, 50%, 70%, 85% or smaller or intermediate or larger percentages.

Figure 8F:
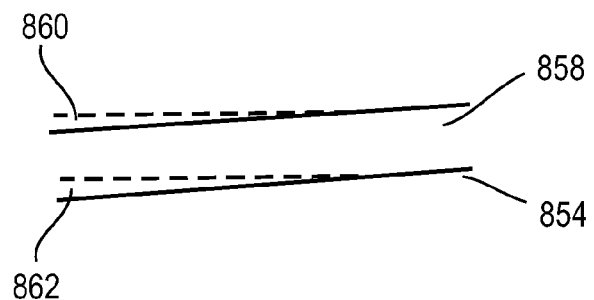
FIG. 8F illustrates a further variant of the mechanism of FIG. 8C, according to some embodiments of the invention.

FIG. 8F shows a variant in which the entire slot opening of a channel 856 is rotated relative to the channel. In general, the rotation is relatively small, for example, less 30 degrees, 20 degrees, 10 degrees, 5 degrees, 2 degrees or smaller or intermediate angles. Optionally, the center of the rotation is near the center of the channel. Alternatively, the center may be near an end of the channel. Optionally, however, channel 856 can snugly engage the wire and prevent bodily motion of the wire in any direction and/or allow application of mechanical torque thereby. Optionally, such engagement is provided even when part of the channel that snugly engages holds the wire itself includes a distortion element (e.g., part of a recess). As shown, recesses 858 and 862 are defined and match protrusions 860 and 864.

Figure 8G:
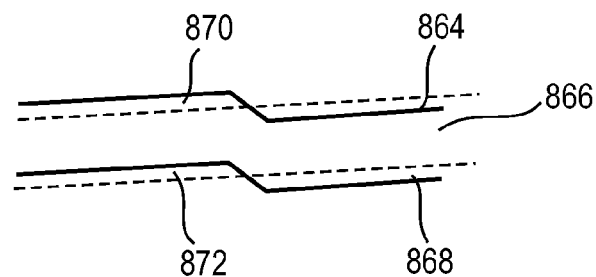
FIG. 8G illustrates a channel with an overlying set of protrusions/recesses, according to some embodiments of the invention.

FIG. 8G shows a channel 866 with an overlying set of protrusions/recesses that defines a crocked entryway. Bending at the crooked point is expected to be unlikely. In the example shown projections 864 and 872 are defined and which match recesses 868 and 870.

Figure 8H:
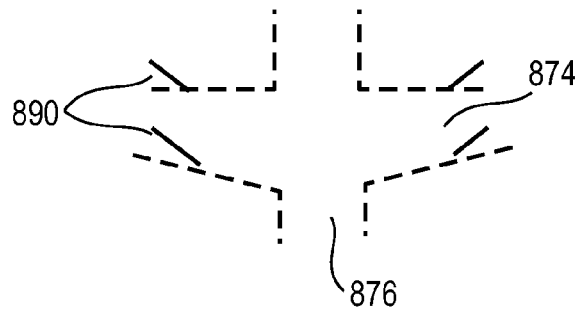
FIG. 8H illustrates a channel design suitable for two crossed channels/slots, according to some embodiments of the invention.

FIG. 8H shows a design suitable for two crossed channels/slots 874 and 876, in which a first wire retainer 878 is formed at one side of channel 874 and a second wire retainer 890 is formed at an opposite side of channel 874.

Figure 8I:
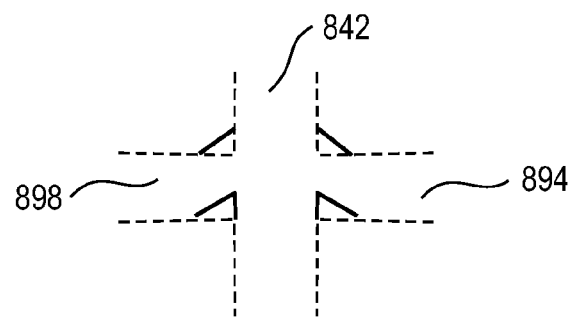
FIG. 8I illustrates a further variant, in which wire retainers are formed at a junction of a channel and a slot, according to some embodiments of the invention.

FIG. 8I shows a variant in which wire retainers 898 and 896 are formed at a junction of channel 894 and a slot 892. Optionally, the protrusions and/or recesses of one or both retainers extend into both channels (e.g., at the junction) and thereby allow both 892 and 894 to operate as channels.

In the embodiments shown in FIGS. 8H and 8I, the channel (894,874) are bi-angulated channels, but a similar design may be used with straight channels.

It is a particular feature of some embodiments of the invention, that the protrusions require a material thickness of less than 50%, less than 30%, less than 10% or intermediate amounts of the depth of the target channel.

Alternative Distortion Based Bracket Designs

Figure 9A:
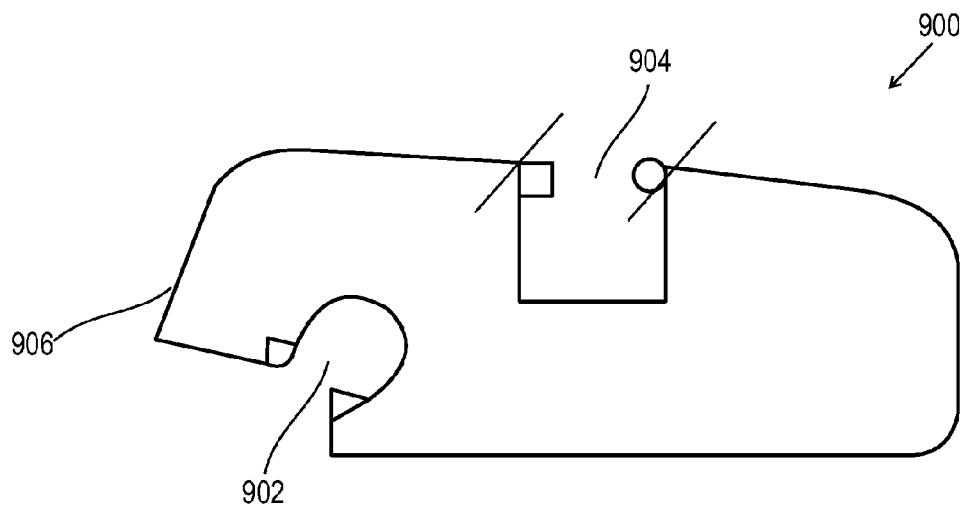
FIG. 9A illustrates an exemplary bracket, wherein one side channel is provided with an optional overhang/tiewing and a square channel in a center of the bracket. according to some embodiments of the invention.
Figure 9B:
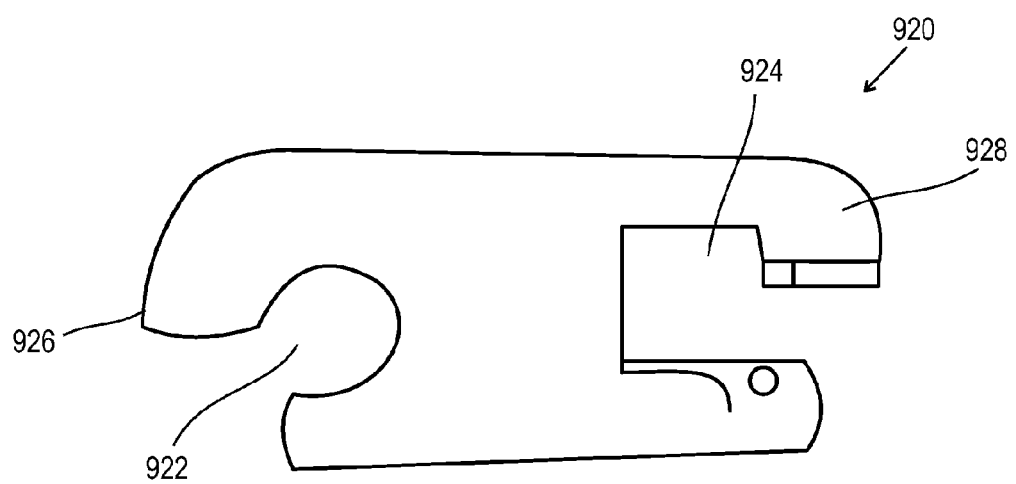
FIG. 9B illustrates an exemplary bracket, wherein a square channel defines an overhang/tiewing, according to some embodiments of the invention.

FIGS. 9A and 9B illustrate exemplary brackets with both a distortion-based round wire holder and a distortion based square wire holder, in accordance with exemplary embodiments of the invention. In some embodiments, the square wire holder is used for a round wire. Any of the cannels may be split as described above. Optionally or alternatively, slots and/or wire guides may be added.

FIG. 9A shows a bracket 900 including only one side channel 902 with an optional overhang/tiewing 906 and a square channel 904 in a center of the bracket.

FIG. 9B shows a bracket 920 with a side round channel 922 with an optional overhang/tiewing 926 and a square channel 924 at an opposite side of the bracket and defining an overhang/tiewing 928.

Additional Exemplary Bracket Features

Figure 12A:
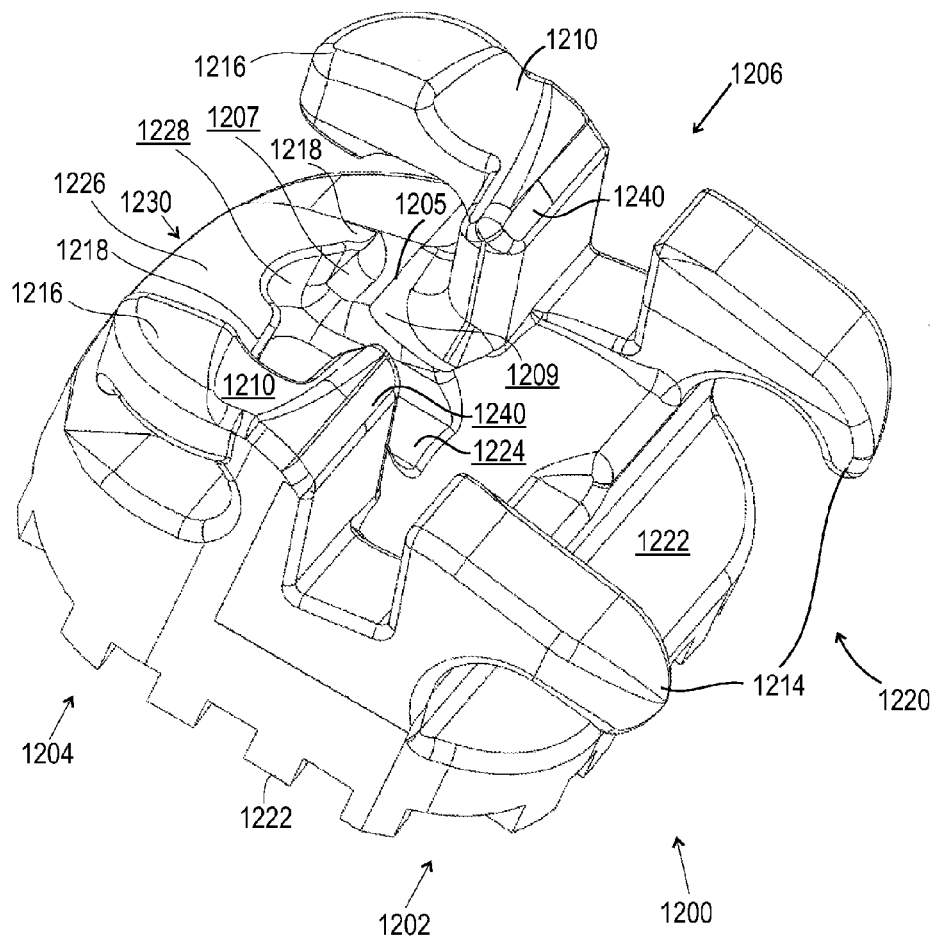
FIG. 12A is a perspective view of a bracket in accordance with an alternative embodiment of the invention.
Figure 12B:
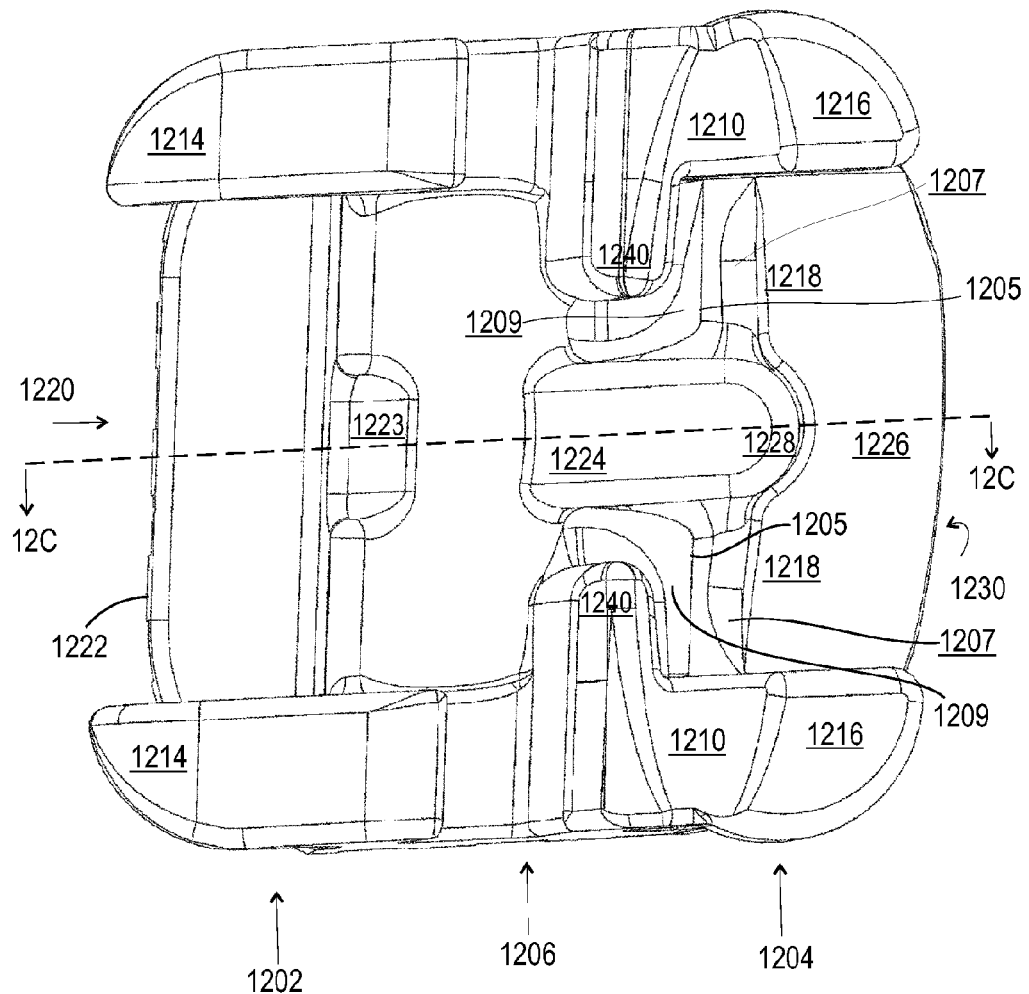
FIG. 12B is a top view of the bracket of FIG. 12A, according to some embodiments of the invention.
Figure 12C:
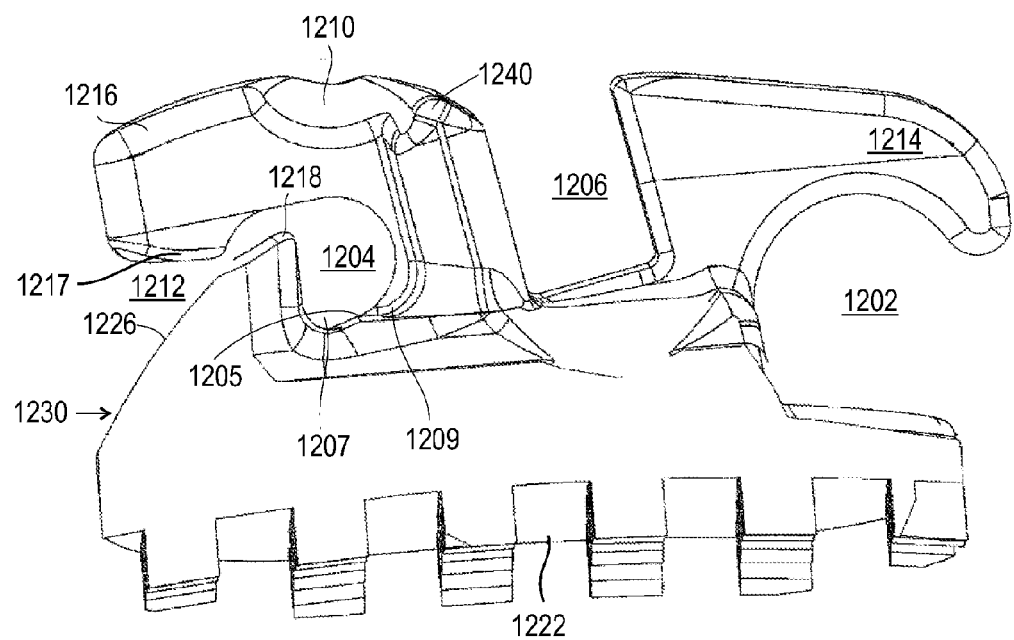
FIG. 12C is a cross-sectional view of the bracket of FIG. 12B, taken in the direction of arrows 12C-12C therein, according to some embodiments of the invention.

FIGS. 12A-12C are views of a bracket 1200 in accordance with an alternative embodiment of the invention. As shown, bracket 1200 includes a first, self ligating channel 1204, which is optionally split into two parts, each is capable of ligating a wire. Optionally, the self-ligating mechanism includes an interference element 1230 shared by and/or place between two channel portions. In the embodiment shown, bracket 1200 includes a base 1222, a square-wire channel 1206 and/or a second non-self ligating channel 1202. As noted herein, each of these channels can be according to other designs as described herein, for example, one or both being omitted or being self-ligating of this or other design. In an exemplary embodiment of the invention, there are no moving parts, for either ligating or wire removal. Optionally, channel 1202 may also include a central (or otherwise) interference element, for example an element which is sized for self-ligating only a single wire diameter. This may also be useful in other bracket designs. In contrast, channel 1204 (and some other self-ligating channels described herein) is optionally suitable for self-ligating multiple wire sizes, for example, over a range of 30%.

FIG. 12A is a perspective view of bracket 1200. FIG. 12B is a top view and FIG. 12C is a cross-sectional view of bracket 1200 along the line marked in FIG. 12B, and showing a view along channel 1204 and possibly better illustrating the interaction between interference element 1230 and channel 1204.

Referring specifically to FIG. 12C, it can be seen that a wire in wire channel 1204 is surrounded substantially from four sides, for example, to an extent of at least 70%, 80%, 90%, 95%, 99% or more of completeness of boundary. On three sides, the channel is surrounded by wings 1216, and on a fourth side, channel 104 is bounded by interference element 1230 (and possibly in part of a protrusion 1217 of wing 1216, both described below). This is similar, in some ways to the design of channel 104 in FIG. 1A. However, in an exemplary embodiment of the invention, the boundary extent is provided in two parts, a first part, under wings 1216, in which only three parts of the channel are bounded and a fourth part, adjacent interference element 1230, where only two sides are bounded. As will be shown below, in some cases, a shoulder 1240 of a wing 1216 acts as a wire retaining element, for example, if it includes an overhang so as to define a wire path.

In an exemplary embodiment of the invention, lateral separation along channel 1204 allows wire bounding from all four sides while reducing the thickness of the bracket, for example, as compared to a spiral. In an exemplary embodiment of the invention, the wings prevent wire motion away from base 1222 and the tooth. In an exemplary embodiment of the invention, the extent of protrusion of shoulder 1250 into a slot 1220 is selected so as to provide a desired amount of bending to the wire (e.g., by narrowing slot 1220) and thus provide a desired amount of angle changing force.

In an exemplary embodiment of the invention, a same interference element 1230 acts to ligate a wire in both halves of channel 1204. In other embodiments, a different side (e.g., a section 1218) on each side of interference element 1230 acts for each channel half. Optionally, one of the sections 1218 is omitted, however, this may reduce the functionality of the bracket. Where a wire passes in both channel halves, both sections 1218 may be active. In other embodiments, interference element 1230 is provided closer to the edge of bracket 1200 than the wings In the embodiment shown, wings 1216 are narrow relative to the width of the bracket, possibly allowing more room for wire manipulation, for example, as shown with respect to FIGS. 13A and 13B, below. For example, each of wings 1216 may be less than 40%, 30%, 20% or intermediate percentages of the bracket width. Optionally or alternatively, interference element 1230 may be, for example, between 10% and 40% of the bracket width, for example, about 20%. In an exemplary embodiment of the invention, there is no overlap (when viewed form above) between wings 1216 and interference element 1230. Alternatively, a small overlap, for example, 10% or 20% by width of the wing, is provided. Alternatively, a space, for example, 10%, 20%, 30% or more of the width of the wing is provided between wing 1216 and interference element 1230 (in a top view). In some embodiments, interference element 1230 is considered to start from where it reaches to a height of at least 10%, 20%, 30% or 40% of the extent of the side to be bounded.

In the specific embodiment shown, an optional ramp structure 1226 is provided to help guide a wire into channel 1204. In use, a wire is provide at a base of bracket 1200, and guided up ramp 1226. A tool (not shown) may be used to guide one or more parts of the wire under wings 1216. Optionally, one or both of wings 1216 includes a lower protrusion 1217 which serves to resist retrograde movement of a wire and/or is curved to match a curve of incline 1226 so as to guide the wire into channel 1204. When pulled sufficiently, the wire will pass sections 1218 and fall into channel 1204 along its entire length. Such a ramp may be provided in other embodiments where a wire is distorted to fit into a channel. In an exemplary embodiment of the invention, wires are inserted into or removed from a bracket by distorting the wire locally a small amount, for example, below its yielding point.

Another optional feature shown is a recess series 1228, 1224 and/or 1223, which lie along a transverse slot 1220, one or both of which can guide the insertion of a tool on either side of the wire to assist in removal thereof. In an exemplary embodiment of the invention, the tool alluded to is a thin curved or bent tube or flat piece of metal, for example, a handle with a hook or a pair of pliers. Optionally, the hook matches the recess so that the recess(es) can act as a fulcrum for moving the wire. Optionally or alternatively, the ramp includes a slot on its face (not shown) for positing a tool between the wire and the ramp. Such a slot can also include a depression to act as a resting point for a levering tool. In one embodiment, a tool is placed so it lies up the ramp and engages recess 1228, which point where the ramp meets the recess acts as a fulcrum. Other implementations will have fewer than all the recesses and/or not include the slot. In an exemplary embodiment of the invention, one or more of the recesses act as a visual aid, for example, to identify an alignment of the bracket with the vertical and/or the tooth.

While the ramp is shown as being substantially linear, it may be concave or convex. Optionally or alternatively, the recess 1208 may be a straight edge, concave or convex, depending on the implementation.

Optionally, interference element 1230 overhangs recess 1228.

In an exemplary embodiment of the invention, instead of recess 1228 there is provided a protrusion which lifts the wire inserted in the channel away form the surface of the tooth. Optionally, this lifting helps in ligating said wire. It is noted that in some embodiments of the invention, slipping of the wire is allowed and/or desired.

In an exemplary embodiment of the invention, at least some of the recesses, for example, recess 1224 underlying channel 106 serve to allow flexing of a wire contained in the channel. This may be useful, for example, in the case of a lingually blocked-out tooth. Having an essentially flat slot floor across the mesial-distal width of the bracket increases binding and friction in such cases where the arch wire can't flex within the bracket as needed to accommodate early treatment conditions.

Optionally, the outsides of wings 1216 are rounded. In some embodiments, the slots that divide the channels are not perpendicular to one or more of the channels (e.g., self ligating or friction based). Optionally or alternatively, the bracket is not symmetric left to right.

In some embodiments of the invention, a stanchion is located inside transverse slot 1220, for example, to serve instead of shoulders 1240, for example, in the form of an upright rod or other protrusion.

Referring to FIG. 12C, channel 1204 is optionally a bi-position channel with two natural wire positions. A cusp 1205 optionally defines two sides, 1207 and 1209, with the wire lying either in one side or the other, depending on where the rest of the wire continues to (e.g., the other channel portion, above the wing or through channel 1206.

As will be shown below with respect to FIGS. 13A and 13B, wire guiding recesses 1210 may be formed on an outer surface of the wings, for example, facing away from base 1222 and/or on their underside, facing the base and/or interference element. Optionally, as shown, locations where a wire is meant to pass are smoothed and/or recessed.

In an exemplary embodiment of the invention, while wings 1216 may be narrow, they include shoulders 1240, which may be used to limit the motion of a wire that passes from channel 1204, through slot 1220 into slot 1206. In an exemplary embodiment of the invention, such limiting acts instead of or together with section 1218 to prevent the wire from escaping the bracket. Optionally (not shown), shoulders 1240 are undercut so they at least slightly overhang slot 1220.

In an exemplary embodiments (and also as applicable to other designs described herein), the width (O-G) of the bracket is less than 0.140 inches, less than 0.0126 inches, less than 0.121 inches or less than about 0.110 inches. Optionally or alternatively, the width (M-D) of the bracket is of similar sizes, or smaller (may depend on teeth), for example, less than 0.120 inches, less than 0.090 inches or less than 0.080 inches. Optionally or alternatively, the thickness of the bracket (height away from tooth surface) is less than 0.140, less than 0.0100, less than 0.080, less than 0.060, less than 0.040, or intermediate sizes. In an exemplary embodiment of the invention, each channel portion of channel 1204 is between 0.020 and 0.040 long. In an exemplary embodiment of the invention, the bonding pad of the base is about the size of the body of the bracket, or, for example, within 10% or 20% in extent, optionally smaller than the bracket. In an exemplary embodiment of the invention, each part of channel 1204 is angulated 5 degrees, so as to define a V shape generally culminating at recess 1228.

In an exemplary embodiment of the invention, the bracket is designed to provide over corrections, for example, 3°, 5°, 7°, 10°, 15°, 20° or 30° or other, smaller, intermediate or greater degrees of angle corrections. It should be noted that a same bracket can provide multiple values of correction angles, by changing the wire and/or moving the wire between guides and/or addition additional wires.

In an exemplary embodiment of the invention, the tie wings (e.g., wings 1216) are about 0.024 inch, for example, between 0.04 and 0.027, for example, between 0.036 and 0.022.

In an exemplary embodiment of the invention, a bracket is formed of a 17-4 PH MIM alloy.

In an exemplary embodiment of the invention, the bracket is designed so that for a stainless steel wire, a deflection of about 0.015 inch is designed for. Other deflections, for example, 0.010, or 0.020 or intermediate may be allowed. In some cases, low deflections result in reduced efficiency and high deflection result in wire yield.

In an exemplary embodiment of the invention, the bracket is designed so that forces of less than 10 pounds, less than 5 pounds, less than 3 pounds or intermediate values are needed to deflect the wire and fit it into a self-ligating channel.

In an exemplary embodiment of the invention, the sizes of the various elements in the bracket may be modified for comfort, aesthetics and/or to match a tooth size. Optionally or alternatively, the sizes are set, at least in part, by functionality. In an exemplary embodiment of the invention, the parameters of the rectangular channel (in this or other embodiments) are set by Roth or MBT methodology. Optionally, a set of 14 brackets is provided per measurement set. Optionally, only the rectangular channel is varied. Alternatively, if, for example, the other cannels are used to complete the treatment, they may be set for a particular desired measurement.

In an exemplary embodiment of the invention, channel 1204 is sized for using, for example, a 0.014 inch NiTI super elastic wire, then progressing to a 0.012 inch diameter stainless steel and then to a 0.014 inch diameter stainless steel wire. Optionally, the channels and slots are positioned so that such wires will be self-ligated, while not distorting any wire beyond yield. In an exemplary embodiment of the invention, the wires used have a range of Young's modulus of between 7,000,000 to 26,000,000. In an exemplary embodiment of the invention, one or more parts of the bracket may be customized during use, for example, using a high-speed bur. In one example, if ramp 1226 is too high, it may be lowered using a burr or other tool.

Figure 13A:
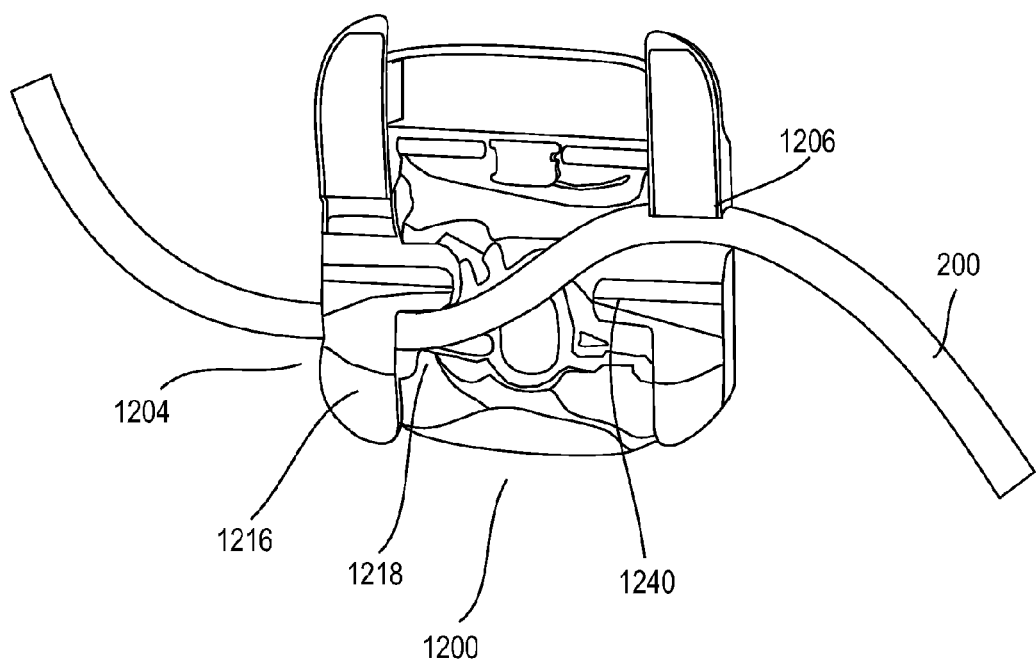
FIG. 13A illustrates a use of the bracket of FIGS. 12A-12C, in accordance with an exemplary embodiment of the invention.
Figure 13B:
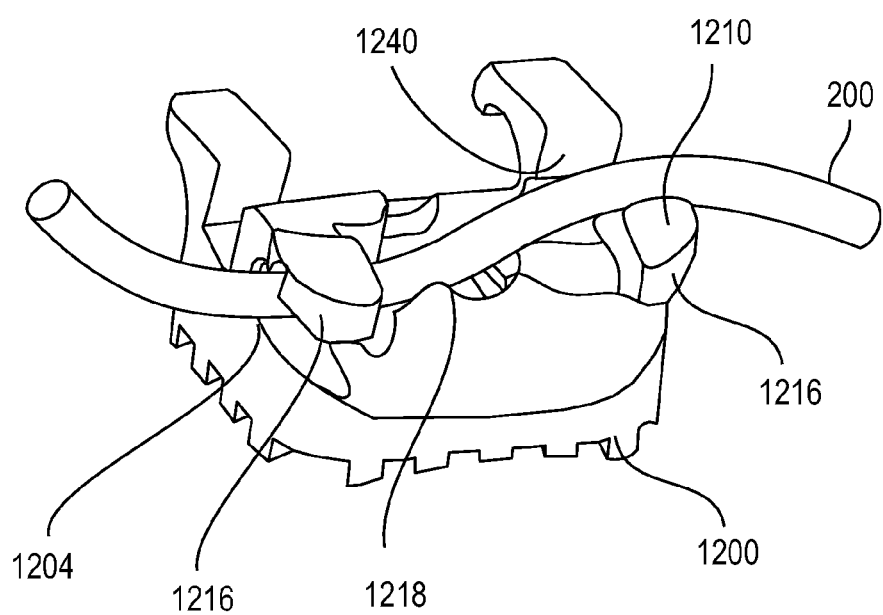
FIG. 13B illustrates a use of the bracket of FIGS. 12A-12C, in accordance with an alternative exemplary embodiment of the invention.

FIGS. 13A and 13B illustrate uses of the bracket of FIGS. 12A-12C, in accordance with exemplary embodiments of the invention FIG. 13A shows a wire 200 which applies torque to a tooth (to which the bracket is optionally attached straight), by lying partly in channel 1204 and partly in channel 1206. In an exemplary embodiment of the invention, ligation is provided by cooperation of section 1218, wing 1216 and optionally shoulder 1240, with the elasticity of the wire.

In an exemplary embodiment of the invention, the inside edge of channel 1206 is smoothed. This may allow a greater bias angle.

In an exemplary embodiment of the invention, the bracket is designed to provide a bias angle which reflects the angle between the wire existing the bracket (at the rectangular slot). Optionally, wings 1216 are made narrower, so this angle can be greater. For example, given a 0.019-wide slot (typical width of a 0.018 slot); a M-D tie wing width of 0.032; and an archwire diameter of 0.014, about 7-8 degrees of bias angle are attainable. Further narrowing of wings 1216 and/or controlling of wings 1240 can allow a greater bias angle, for example, 10 degrees, 15 degrees or more, to be achieved.

FIG. 13B shows a wire 200 which applies rotation to a tooth (to which the bracket is optionally attached straight), by lying partly in wire guide 1210 above a second part of channel 1204. In an exemplary embodiment of the invention, ligation is provided by cooperation of section 1218 and two wings 1216, with the elasticity of the wire.

Adjustable Wire Retainer

It is a particular feature of some embodiments of the invention that the bracket includes no moving parts. Optionally, however the bracket can be configured after use.

Figures 10A, 10B:
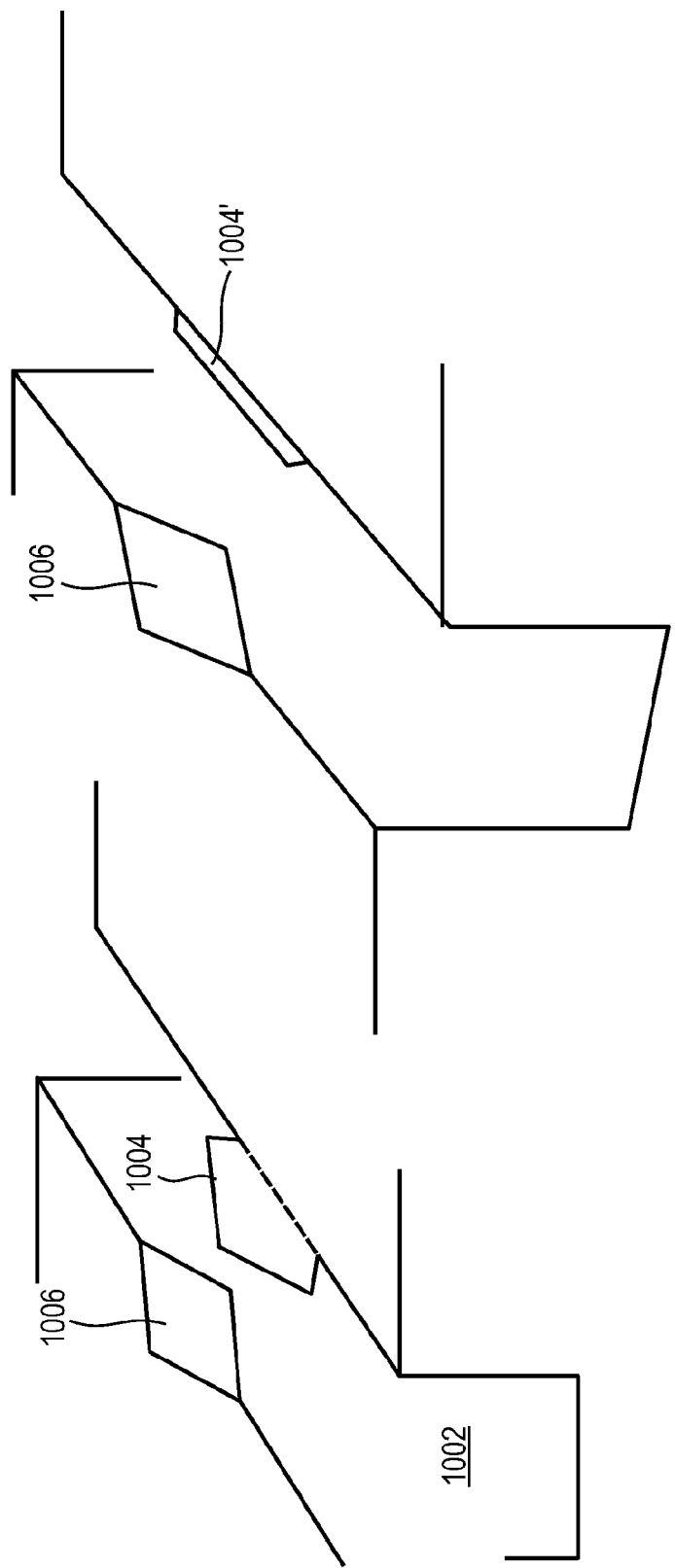
FIG. 10A illustrates a reconfigurable wire holder, in accordance with an exemplary embodiment of the invention.
FIG. 10B illustrates a reconfigurable wire holder of FIG. 10A, wherein a projection has been reshaped, according to some embodiments of the invention.

FIGS. 10A and 10B illustrate a reconfigurable wire holder, in accordance with an exemplary embodiment of the invention. A channel 1002 has an interference base distortion wire retainer, for example as described above, using a recess 106 and a protrusion 1004. Protrusion 1004 is made large enough that a relatively flexible and/or small diameter wire will be retained in channel 1002. Optionally, when it is desired to change to a thicker and/or less flexible wire, projection 1004 is reshaped, for example, by breaking along a break-line, or by abrasion, to yield a smaller protrusion 1004' which can be managed by the thicker and/or more rigid wire.

Figure 10C:
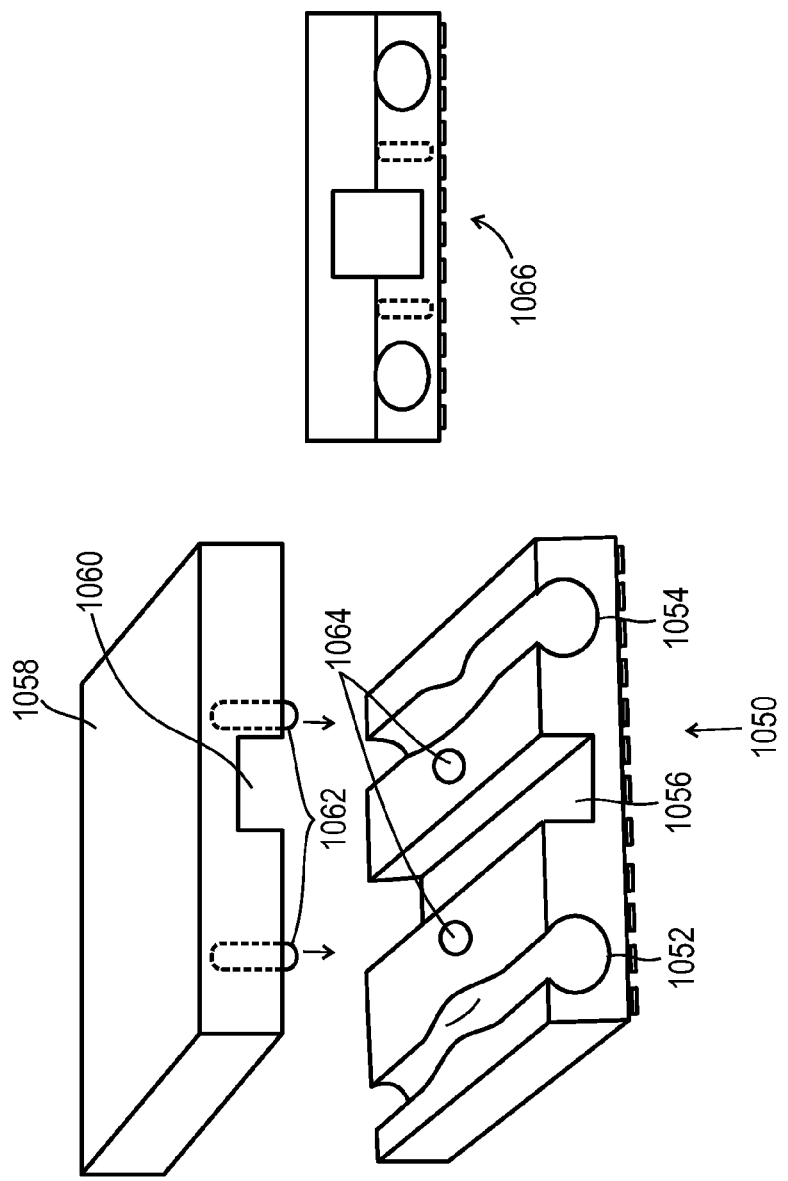
FIG. 10C illustrates a wire holder adapted for adding an element thereto, in accordance with an exemplary embodiment of the invention.

FIG. 10C illustrates a bracket 1050 adapted for adding an element thereto, in accordance with an exemplary embodiment of the invention. In this embodiment, bracket 1050 has one two or more shallow distortion based channels (1052, 1054). A residual straight channel 1056 is optionally provided. This allows a shallow/thin and/or smoother bracket to be provided. If and when an additional channel is desired, for example, for final corrections, an element 1058 is added which defines an additional channel. In the embodiment shown, the additional channel is formed by a matching up of residual channel 1056 and a recess 1060 in element 1058. In the embodiment shown, element 1058 covers all of bracket 1050, but this is not essential. In the embodiment shown, element 1058 attaches to bracket 1050 using a pin (1062) and aperture (1064) mechanism, and optionally adhesive. Optionally or alternatively, a part of element 1058 (e.g., a mushroom-shaped element with a widening tip and a narrow neck) fits in a channel (e.g., 1052 or 1054) of bracket 1050, optionally being inserted by sliding. Reference 1066 indicates an assembled configuration.

Combination Brackets

The above description has provided a range of wire retainers, wire guides, elastic holders and relative positions thereof. A bracket in accordance with an exemplary embodiment of the invention may include any combination and multiplicity of instances of the above described features (e.g., 2, 3, 4, 5, 7 or more individually accessible wire retaining and/or wire guiding elements). In an exemplary embodiment of the invention, a bracket includes wire retainers as known in the art, together with the various inventive retainers and/or other features described herein.

Figure 11A:
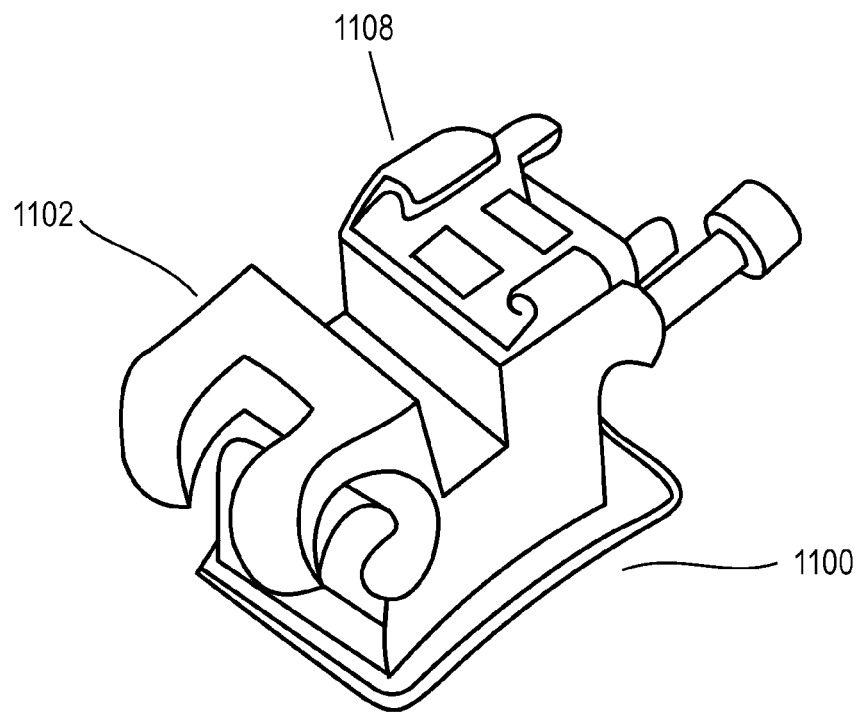
FIG. 11A illustrates a bracket which combines a labyrinth-like section and a lockable standard channel section, in accordance with exemplary embodiments of the invention.
Figure 11B:
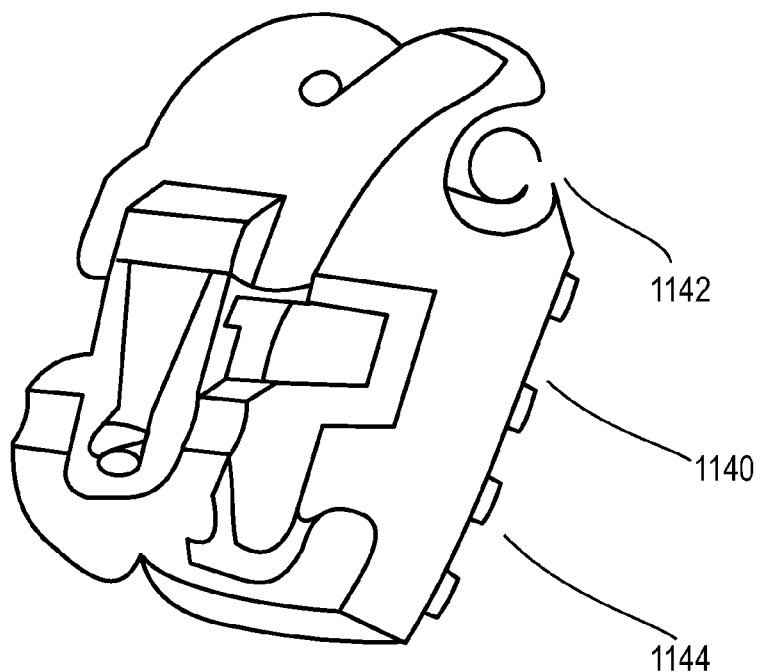
FIG. 11B illustrates a bracket which combines a labyrinth-like section and a lockable standard channel section, using an elastic clip, in accordance with exemplary embodiments of the invention.

FIGS. 11A and 11B illustrate brackets which combine wire holding mechanism with moving parts with wire holding mechanism with no moving parts, in accordance with exemplary embodiments of the invention. FIG. 11A shows a bracket 1100 including a labyrinth-like section 1102 and a lockable standard channel section 1104, using a locking mechanism with a sliding clip. Optionally, a prior art or other movable locking mechanism is used for a channel with a distortion-based wire retention mechanism. FIG. 11B shows a bracket 1140 with a labyrinth-like section 1142 and a lockable standard channel section 1144, using an elastic clip.

Planning

In an exemplary embodiment of the invention, there is provided a computer program for visualizing forces applied to teeth using the brackets as described above and/or for planning, optionally automatically suggesting, orthodontic plans. Optionally, such suggestion is by methods known in the art, such as rule application and searching for optimal solutions, using a simulation of the teeth in question and the available force application mechanisms.

Optionally or alternatively, the brackets are provided with a booklet (or website or software) illustrating different force application possibilities for individual brackets and sets of brackets, optionally with supporting elements, such as springs.

In an exemplary embodiment of the invention, the process of planning (e.g., manual and/or automatic) is changed over the art, at least in some cases, due to one or more of: ability to provide more exact forces, lesser need to move brackets, ability to more specifically target teeth and/or ability to apply forces where not possible before.

Aesthetics

As noted above, various features may be provided in a bracket in accordance with some exemplary embodiments of the invention, to improve aesthetics, for example, hiding of wires, palatal brackets, providing smaller and/or thinner brackets, selecting fewer or more channels and/or slots, and/or supporting the use of thinner wires Optionally or alternatively, the aesthetics, the various features may be selected in a bracket to improve hygiene (e.g., fewer points to collect dirt) and/or reduce risk or inadvertent peeling of a bracket (e.g., by providing fewer suitable leverage points with a reduced moment).

Sizes

In an exemplary embodiment of the invention, the bracket is designed for wires of size 0.012 inch, 0.014 inch or 0.018 inch. In an exemplary embodiment of the invention, smaller diameter wires are used as multiple wires can be used simultaneously. This may allow the bracket to be thinner and/or smaller in area, for example, 50% thinner than existing brackets.

Materials

In an exemplary embodiment of the invention, the bracket is formed of various materials, for example, metal, plastic or ceramic. Optionally, part of the bracket is made somewhat elastic, for example, the protrusions of the wire retainers or tiewings. Alternatively the entire bracket (or parts retaining wires) is rigid, for example, being formed of a ceramic element, optionally mounted on a base.

Optionally, metal and plastic brackets are made smaller than ceramic brackets.

This may affect the size and shape of the labyrinth-like channel, if any.

Sets

It is a particular feature of some embodiments of the invention that a bracket may be used together with standard tools and techniques of the orthodontic trade, in some cases, with improved effect.

In one example, a bracket or set of brackets may be customized (e.g., by milling a standard form or by custom forming). For example, each bracket in a set of brackets can have a different central standard channel angle.

In another example, springs and elastic elements may be mounted as known in the art. Optionally, such springs are attached to features of the bracket, such as the wings or intersections between cannels and slots or in channels. Optionally, one or more springs are designed for use and mounting on the brackets as described herein and may be sold therewith.

In another example, the cannels may be compatible with various standard (or custom) wire sizes and elasticity and/or be formed to support using a chain elastic.

In an exemplary embodiment of the invention, a range of bracket types are available for a used, for use in different situations. Optionally, the brackets are sold in sets for a use. Optionally or alternatively, each bracket is sold separately, optionally in multiples.

In an exemplary embodiment of the invention, no special tools are needed for using the brackets described herein. Optionally, a wire twisting tool is provided for the distortion based channels. Optionally or alternatively, a plier with a curved back tip is used for lingual brackets, for wire manipulation.

General

It is expected that during the life of a patent maturing from this application many relevant features like wires and bracket material or biology factors that may influence teeth movement will be developed and the scope of these terms are intended to include all such new technologies a priori.

As used herein the term "about" refers to ±10%. The term "substantially" generally refers to an effect that is clinically meaningful.

It should be noted that many designs are possible. Of particular interest in some embodiments of the invention are designs which provided clinically acceptable or useful behavior of the bracket in straightening teeth.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. For example, a first bracket design may include channel designs or slot designs of a different bracket, or adaptations of a first bracket for certain situations may be applied to a different bracket. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. An orthodontic self-ligating bracket comprising: a body having a base configured for attaching to a tooth, said body having a gingival side and a non-gingival side, wherein said bracket is configured to be attached to a tooth with said gingival side nearer a gumline than said non-gingival side; rigid right and left self-ligating wire guide channels formed in said body and spaced closer to one of said gingival side and said non-gingival side than to said other of said gingival side and said non-gingival side, wherein said rigid right and left self-ligating wire guide channels are each sized and shaped to retain a wire therewithin;
   a slot formed in said body between said rigid right and left self-ligating wire guide channels, wherein said slot is wide enough such that a wire can enter said slot in a direction parallel to the tooth axis and can bend and enter one of said rigid right and left self-ligating wire guide channels;
   wherein each of said rigid right and left self-ligating wire guide channels has a wire insertion direction into a respective wire entry pathway, said wire insertion direction being parallel to said base;
   wherein said wire entry pathway of each of said rigid right and left self-ligating wire guide channels is at least partly bounded by respective right and left wing portions, each of said wing portions forming a boundary on three sides of said respective rigid self-ligating wire guide channel;
   an interference element in said slot, said interference element forming a boundary of a side of said rigid right self-ligating wire guide channel in said direction, said boundary formed by said interference element not substantially overlapping said boundary formed by said right wing portion, wherein said boundary formed by said interference element interferes with removal of the wire from said rigid right self-ligating wire guide channel;
   wherein said bracket is configured to provide ligation by engagement of the wire with said rigid right self-ligating wire guide channel, a side of said interference element, and said left wing portion; and a non-self-ligating wire guide channel configured for retaining therein a wire having a rectangular cross section, said non-self-ligating wire guide channel being disposed closer to said other of said gingival side and said non-gingival side than said rigid right and left self-ligating wire guide;
   wherein said rigid right self-ligating wire guide channel has at least one distortion in said wire entry pathway, said at least one distortion including at least one of a protrusion and a recess configured to retain a wire in said rigid right self-ligating wire guide channel.

2. The bracket according to claim 1, wherein said rigid right self-ligating wire guide channel has a first axial portion bounded on three sides by said right wing portion.

3. A bracket according to claim 2, wherein said bracket provides at least three tooth movement functions using said rigid right and left self-ligating wire guide channels.

4. A bracket according to claim 2, wherein said rigid right and left self-ligating wire guide channels are angulated.

5. A bracket according to claim 2, wherein said rigid right and left self-ligating wire guide channels are arranged to self-ligate for a range of different round wire diameters over a range of at least 1:1.2.

6. A bracket according to claim 2, wherein said first axial portion is less than 80% of a length of said rigid right self-ligating wire guide channel.

7. The bracket according to claim 1 wherein said rigid right and left self-ligating wire guide channels are arranged to selectively provide a tooth movement function selected from a group including at least two of tipping, rotation, angulation and torque to a tooth on which said bracket is mounted by varying a location of at least one wire between said rigid right and left self-ligating wire guide channels and anchoring the at least one wire off of said tooth.

8. A bracket according to claim 7, wherein said rigid right and left self-ligating wire guide channels are arranged to provide at least two different values of at least one of said tooth movement functions, without moving the bracket and by moving the wire.

9. A bracket according to claim 8, wherein said bracket provides two different non-zero values for at least two of said tooth movement functions.

10. A bracket according to claim 1, wherein said interference element extends substantially perpendicular to said tooth surface.

11. A bracket according to claim 1, wherein at least one of said wire guide channels has a wire insertion direction substantially away from a tooth surface.

12. A bracket according to claim 1, wherein said slot is positioned to function as a buccal channel.

13. A bracket according to claim 1, wherein said interference element blocks less than 80% of a width of said side.

14. A bracket according to claim 1, wherein a length of said interference element blocking said wire insertion direction is less than 80% of a functional length of said rigid right self-ligating wire guide channel, within which a wire lies.

15. A bracket according to claim 1, comprising an inclined segment positioned for guiding a wire up and past said interference element into said rigid right self-ligating wire guide channel.

16. A bracket according to claim 1, wherein a self-ligating mechanism is an interference element.

17. A bracket according to claim 1, wherein said slot is wide enough for a stainless steel wire that self ligates in said rigid right self-ligating wire guide channel to bend into the slot at an angle.

18. The bracket according to claim 17 wherein the bent wire passes through the slot and exits.

19. A bracket according to claim 1, wherein at least one of said right and left wing portions defines at least one depression formed therein outside of a respective at least one of said rigid right and left self-ligating wire guide channels.

20. The bracket according to claim 1 wherein a wire passing through said rigid right self-ligating wire guide channel does not pass through said rigid left self-ligating wire guide channel.

21. The bracket according to claim 1 wherein the inner edges of sa rigid right and left self-ligating wire guide channels comprise rounded edges support wire bending at the edges of said rigid right and left self-ligating wire guide channels.

22. A bracket according to claim 1, wherein said interference element forms a boundary on only two sides of said rigid right self-ligating wire guide channel, at least a portion of said boundary formed by said right wing portion overlapping with at least a portion of said interference element.

23. A bracket according to claim 1, wherein said rigid left and right self-ligating wire guide channels are asymmetric, said asymmetry characterized by at least one of:
  a. said rigid left and right self-ligating wire guide channels are angulated using different angles;
  b. said rigid left and right self-ligating wire guide channels are unequal in length; and
  c. wing portions on said rigid left and right self-ligating wire guide channels have different configurations.

24. A bracket according to claim 1, wherein said rigid left and right self-ligating wire guide channels are each sized to receive a wire having a diameter configured to provide the bracket with a friction-fit between the wire and said rigid self-ligating wire guide channel after insertion of the wire in said rigid self-ligating wire guide channel.

25. A bracket according to claim 1, further comprising a recess in said body formed under said slot, said recess configured for allowing insertion of a device under a wire retained in said slot.

26. A bracket according to claim 1, wherein at least one of said right and left wing portions includes at least one wire guide formed on an outside surface of said bracket, said at least one wire guide configured for guiding a wire to apply angulation forces to said bracket.

27. A bracket according to claim 1, wherein a lower portion of at least one of said right and left wing portions includes a curved portion having a structure which matches a curved portion of said body, said curved portion on said wing portion and said curved portion of said body configured to guide a wire into a respective rigid self-ligating wire guide channel.

28. A bracket according to claim 1, wherein at least one of said rigid right and left self-ligating wire guide channels includes a working area and a wire entry passageway having a spiral form with said working area substantially at an inside end of said wire entry passageway, said wire entry passageway configured such that there is no straight line vector for passage of a wire from within said working area to outside of said spiral form.

29. A bracket according to claim 1, further including additional right and left self-ligating wire guide channels formed in said body and spaced closer to the other one of said gingival side and said non-gingival side than said right and left self-ligating wire guide channels, said body having said slot formed therein between said additional right and left self-ligating wire guide channels.

30. The bracket according to claim 29, wherein said rigid right self-ligating wire guide channel, said rigid left self-ligating wire guide channel, said additional right self-ligating wire guide channel, and said additional leftself-ligating wire guide channel are adapted to simultaneously hold different wires, and wherein the wires may be held in any one or any combination of six different positions.

31. The bracket according to claim 29 wherein said rigid right and left self-ligating wire guide channels and said additional right and left self-ligating wire guide channels comprise at least one of: an incisal channel for providing tooth alignment control, a gingival channel for providing tooth angulation control, and an edgewise channel for providing tooth tip and torque control.

32. The bracket according to claim 29, said slot configured to allow a wire to run at least partly inside said rigid right self-ligating wire guide channel, through said slot, and at least partly inside said additional left self-ligating wire guide channel.

33. An orthodontic system comprising: the bracket according to claim 29, wherein said rigid right and left self-ligating wire guide channels are located on said gingival side of said bracket, and said additional right and left self-ligating wire guide channels are located on said non-gingival side of said bracket; wherein said slot is configured to allow a wire to run at least partly inside said additional right self-ligating wire guide channel, through said slot, and at least partly inside said rigid left self-ligating wire guide channel; and at least a first wire which runs partly in a rigid self-ligating wire guide channel on said gingival side of said bracket and partly in a wire guide channel which is on said non-gingival side of said bracket.

34. An orthodontic system comprising: the bracket according to claim 1, wherein said rigid right self-ligating wire guide channel includes a groove at the first axial portion thereof, said groove sized and shaped to at least partly receive the wire therein; and a wire configured to run partly in a rigid self-ligating wire guide channel on a first side of the bracket spaced closer to one of said gingival side and said non-gingival side than to said other of said gingival side and said non-gingival side and partly in a self-ligating wire guide channel which is not on the first side of the bracket.

35. An orthodontic system according to claim 34, wherein at least a first wire runs partly in the rigid self-ligating wire guide channel on a gingival side of said bracket and partly in a wire guide channel which is on a non-gingival side of said bracket; and wherein at least a second wire runs partly in one of said rigid self-ligating wire guide channel and said wire guide channel.

36. A method of manipulating a tooth during orthodonty, comprising:
  (a) attaching a self-ligating bracket to the tooth;
  (b) running at least a first wire through at least a first self-ligating guide channel and at least a second wire through at least a second channel in said bracket, wherein the at least first wire runs partly in a self-ligating wire guide channel on a gingival side of the bracket and partly in a wire guide channel which is not on a gingival side of the bracket;
  wherein said at least one of said wire guide channels has a wire insertion direction and an interference element which forms a boundary of a side of said channel in said direction, said running including distorting a wire such that it can enter a wire entry pathway, the wire entry pathway distorted by a distorting mechanism having at least one of a protrusion and a recess, said distorting mechanism further retaining the wire in said wire guide channel; and (c) positioning said at least first and second wires so that they together apply movement forces for two or more of angulation, rotation, torque and tipping of said tooth;

wherein ligation is provided by one of:

cooperation of a bracket section located between left and right channels, a wing located above said left channel, and a shoulder portion of a wing located above said second self-ligating channel; and cooperation of a bracket section located between said left and right channels and wings located above said right and left channels.

37. The method according to claim 36 comprising bending the at least first and second wires into one or more slots in said bracket.

38. The method according to claim 37 comprising passing the bent at least first and second wires through the one or more slots.

39. A method according to claim 36, wherein said running at least a first wire and said running at least a second wire includes distorting at least one of the first and second wire when the at least one of the first and second wire enters into the respective wire guide channel.

40. The method according to claim 36, wherein said running at least a first wire and said running at least a second wire includes running at least the first wire inside at least said left channel and outside at least said right channel.

41. The method according to claim 36, wherein the at least first wire runs above a portion of the right channel.

42. The method according to claim 36, wherein said at least first self-ligating guide channel is split into a left channel and a right channel, wherein said running at least a first wire and said running at least a second wire includes running at least a first wire inside at least said left channel of said first self-ligating guide channel.

* * * * *